(12) United States Patent
Simons-Nikolova et al.

(10) Patent No.: US 9,779,462 B2
(45) Date of Patent: Oct. 3, 2017

(54) COMPUTER-IMPLEMENTED METHOD OF MANUFACTURING A COMPUTER-READABLE STORAGE MEDIUM FOR A REMOTE PATIENT MANAGEMENT SYSTEM

(75) Inventors: Mariana Simons-Nikolova, Bolton, MA (US); Aleksandra Tesanovic, Eindhoven (NL); Harm Jacob Buisman, Eindhoven (NL); Rob Theodorus Udink, Lieshout (NL); Hans-Aloys Wischmann, Henstedt-Ulzburg (DE); Armin Bruege, Boeblingen (DE)

(73) Assignee: Koninklijke Philips N.V., Eindhoven (NL)

( * ) Notice: Subject to any disclaimer, the term of this patent is extended or adjusted under 35 U.S.C. 154(b) by 1730 days.

(21) Appl. No.: 12/947,849

(22) Filed: Nov. 17, 2010

(65) Prior Publication Data
US 2011/0153350 A1      Jun. 23, 2011

Related U.S. Application Data

(60) Provisional application No. 61/287,296, filed on Dec. 17, 2009.

(51) Int. Cl.
*G06Q 50/22* (2012.01)
*G06Q 10/10* (2012.01)

(52) U.S. Cl.
CPC ............. *G06Q 50/22* (2013.01); *G06Q 10/10* (2013.01)

(58) Field of Classification Search
USPC ........................................................ 705/2, 3
See application file for complete search history.

(56) References Cited

U.S. PATENT DOCUMENTS

| | | |
|---|---|---|
| 2003/0014279 A1 | 1/2003 | Roman et al. |
| 2007/0033072 A1* | 2/2007 | Bildirici ............................ 705/3 |
| 2008/0319796 A1* | 12/2008 | Stivoric et al. ................... 705/3 |
| 2009/0070137 A1 | 3/2009 | Haider et al. |

FOREIGN PATENT DOCUMENTS

WO    WO2007117719    10/2007

* cited by examiner

*Primary Examiner* — Sean K Hunter

(57) ABSTRACT

A computer-implemented method of manufacturing a computer-readable storage medium for a remote patient management system with instructions for causing the execution of a care plan comprising a coaching plan. The method comprises: displaying a list of psychological determinants, receiving a selection of a group of psychological determinants chosen from the list of psychological determinants, generating a list of behavioral models using the group of psychological determinants, receiving a selection of at least one selected behavioral model from the list of behavioral models, determining a time line for the global structure of the coaching plan using the at least one selected behavioral model, compiling a coaching object file using the time line, linking the coaching object file to a library of multi-media content to resolve unresolved symbolic links of the time line, integrating the coaching plan into the care plan, and writing the care plan to the computer-readable storage medium.

20 Claims, 19 Drawing Sheets

|  | Stage based on model | Health belief model | Entertainment education | Theory of planned behavior | Self-regulation |
|---|---|---|---|---|---|
| 510 | Duration_Stage (in weeks) | 25 | 12 | 16 | 36 |
| 512 | # Phases_Stage | 3 | 1 | 4 | 6 |
| 514 | Name_Phases _Stage | Perceived severity Perceived benefits Perceived barriers | Edutainment | Intention Attitudes Subjective social norms Perceived behavioral control | Goal Setting Planning Self-monitoring Feedback Relapse Prevention Maintenance |
| 516 | Next stage rule | | Knowledge = true, etc. | | Goal setting = true Planning = true, etc. |
| | Content elements (CoEl) per stage | | | | |
| 518 | videos | | + | | |
| | messages | + | | + | + |
| | quizzes | | + | | + |
| | surveys | + | | + | |
| 520 | Content distribution | | | | |
| | days per week | 2 | 3 | 2 | 4 |
| 522 | Max # of CoEl | | | | |
| | per day | 1 | 1 | 1 | 1 |
| | Design Rules | | | | |
| 524 | Rule1 | No CoEl in the weekends | | | |
| | Rule 2 | The video teaching quiz is sent at least one day later than the the corresponding video | | | |
| | .... | | | | |
| | Rule N | Choose a fixed day of the week of a particular CoEl, e.g., videos every Tuesday | | | |

FIG. 5

| | | CP Authoring Tool, Steps 1-3 of the algorithem | |
|---|---|---|---|
| | Step | Input | Output |
| 702 | 1 | Groups of determinants<br><br>Determinants of compliance<br>- Patient-related (Physiologocal+Psychological)<br>- Therapy-related<br>- Condition-related<br>- Social economic-related<br>- Healthcare system-related | Medical professional selection of a group of determinants for a particular patient, e.g. the patient-related group and in particular the psychologocal determinants<br><br>Patient-related (Physiologocal+Psychological) |
| 704 | 2 | Psychological determinants within patient-related group<br><br>Patient-related determinants (Psychological)<br>• knowledge (HF + co-morbidities)<br>• perceived risk of disease<br>• understanding reason meds & lifestyle changes are needed<br>• attitudes/expectations toward treatment<br>• perceived benefit & barriers to treatment<br>• self-efficacy<br>• motivation<br>• fear of possible adverse effect<br>• fear of dependence<br>• feeling stigmatized by the disease<br>• frustration with healthcare providers<br>• psychosocial stress, anger, anxiety<br>• alcohol or substance abuse | Medical professional selection of a number of determinants, e.g. knowledge and self-afficacy<br><br>Patient-related determinants (Psychological)<br>- knowledge (HF + co-morbidities)<br>- self-efficacy |
| 706 | 3 | List of (behavioral) models that can modify the selected determinants<br><br>Patient-related determinants (Psychological)<br>- knowledge (HF + co-morbidities)<br>- self-efficacy | Medical professional selection of a (combination of) model, e.g. entertainment education and self-regulation theory<br><br>Behavioral Models<br>- Entertainment Education<br>- Health Believe model<br>- Trans-Theoretical Model<br>- Self-Regulation Theory<br>- Theory of Planned Behavior |

FIG. 8

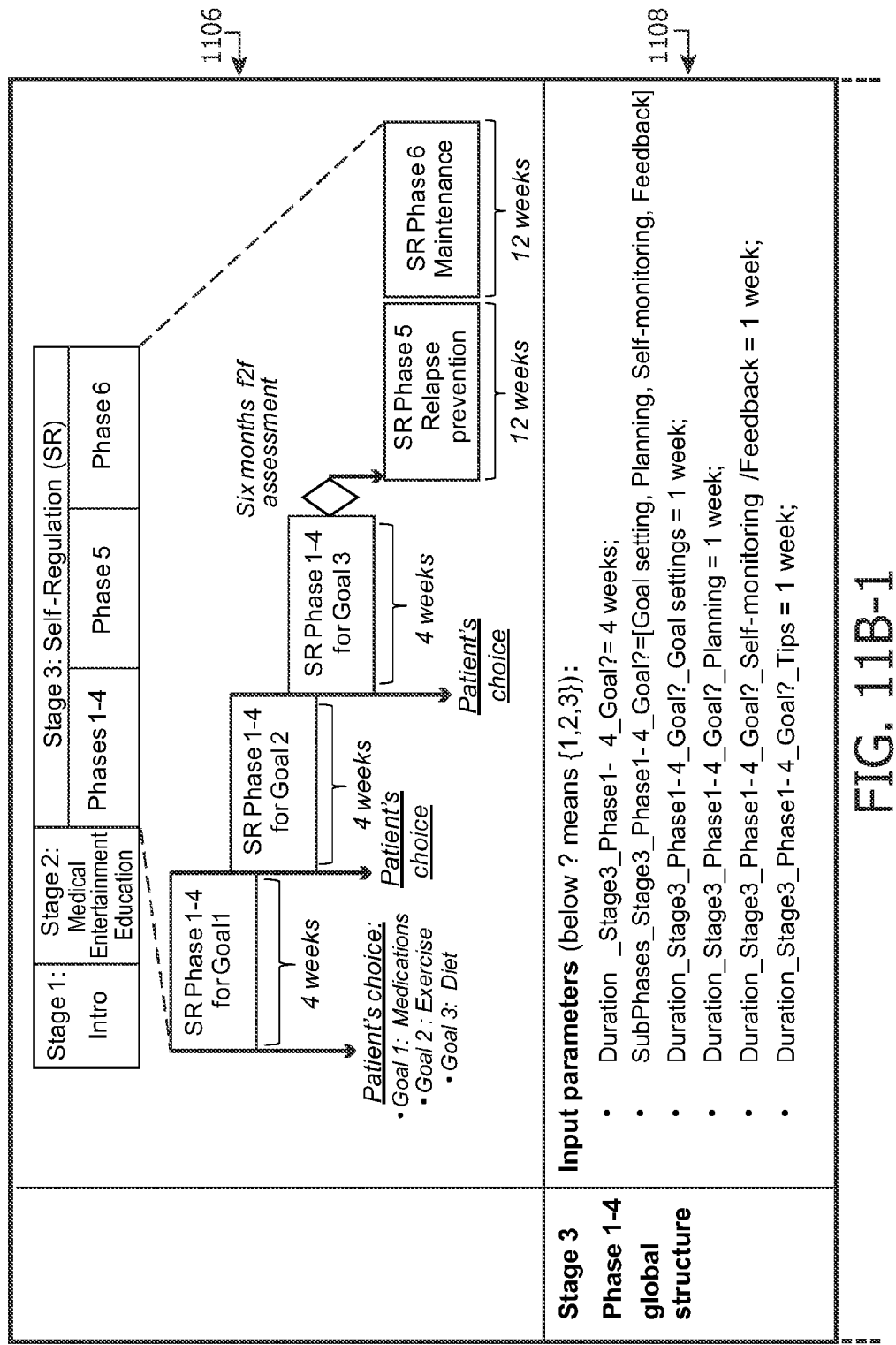

| CP compiler, Step 5 of the algorithm ||
|---|---|
| Stage 1<br>Intro<br>1200<br>1202<br>1201A<br>1201B | Input:<br>• Duration = 2 weeks<br>• Type of content elements [= video]<br>• Content distribution during the week = yes<br>• Max number of content elements per day = 1<br>• Design Rule 1 = no content elements in the weekends;<br>• Design Rule 2 = the first day the patient gets Intro message and Intro video;<br>Output: an exaple of specification for week 1 and 2 |

| | Monday | Tuesday | Wednesday | Thursday | Friday | Saturday | Sunday |
|---|---|---|---|---|---|---|---|
| |  |  ~1203 | |  ~1205 | | | |
| | <br>Intro | Q&A<br>part 1 | | Q&A<br>part 2 | | | |
| | |  ~1206<br>Q&A<br>part 3 | |  ~1207<br>Q&A<br>part 4 | | | |

| Stage 2<br>Edutain<br>-ment<br>1204<br>1213 | Input:<br>• Duration =12 weeks<br>• Type of content elements = [video, teaching quiz]<br>• Content distribution during the week = yes<br>• Max number of content elements per day = 1<br>• Design Rule1 = no content elements in the weekends<br>• Design Rule2 = the video teaching quiz is sent at least one day later than the corresponding video<br>Output: an example of specification for each week |
|---|---|

FIG. 12A

| | Monday | Tuesday | Wednesday | Thursday | Friday | Saturday | Sunday |
|---|---|---|---|---|---|---|---|
| 1214 | Goal setting choice and intro | (video) 1215 | | Goal setting quiz 1216 | Engaging reinforcement message 1218 | | |
| | Monday | Tuesday | Wednesday | Thursday | Friday | Saturday | Sunday |
| 1220 | Planning intro | (video) 1221 | | Planning quiz 1222 | Engaging reinforcement message 1224 | | |
| | Monday | Tuesday | Wednesday | Thursday | Friday | Saturday | Sunday |
| | Self-monitoring intro 1226 | | | | Feedback message 1228 | | |
| | Monday | Tuesday | Wednesday | Thursday | Friday | Saturday | Sunday |
| | Tip Activity 1230 | | Tip Diet 1232 | | Tip Meds 1234 | | |

| Stage 3 Phase 5 | |
|---|---|
| 1236 | Input:<br>• Total duration = 12 weeks<br>• Type of content elements = [interactive message, video, quiz, reinforcement tips message]<br>• Content distribution during the week = yes<br>• Max number of content elements per day = 1<br>• SubPhases_Stage3_Phase5 = [Symptoms, Medications, Exercise, Diet&Fluid]<br>SubPhase is one of [Symptoms, Medications, Exercise, Diet&Fluid] in the next 4 lines<br>• Duration_Stage3_Phase5_SubPhase = 3 weeks;<br>• Schedule_SubPhase_week1 = [1. interactivemessage, 2. video, 3. quiz, 4. reinforcement tips message]<br>• Schedule_SubPhase_week2 = [1. Tip message on barrier 1, 2. Tip message on barrier 2]<br>• Schedule_SubPhase_week3 = [1. Tip message on barrier 3, 2. Tip message on barrier 4]<br>• Design Rule1 = no content elements in the weekends;<br>• Design Rule3 = choose fixed days of week2 and week3 for tip messages; |
| 1238 | Output: an exaple of specification for all 4 RP modules/subphases (symptoms, Medications, Exercise and Diet&Fluid) |

FIG. 12C

| | Monday | Tuesday | Wednesday | Thursday | Friday | Saturday | Sunday |
|---|---|---|---|---|---|---|---|
| 1240 | Intro identified barriers | | 1241 | RP quiz 1243 | reinforcement message 1242 | | |
| | Monday | Tuesday | Wednesday | Thursday | Friday | Saturday | Sunday |
| 1244 | Tip on identified barrier | | | | Tip on identified barrier 1245 | | |
| | Monday | Tuesday | Wednesday | Thursday | Friday | Saturday | Sunday |
| 1247 | Tip on identified barrier | | | | Tip on identified barrier 1251 | | |

Phase 6 of Stage 3

Input:
- Total duration = 12 weeks
- Type of content elements =
  [interactive message, video, quiz, reinforcement tips message]
- Content distribution during the week = yes
- Max number of content elements per day = 1
- SubPhases_Stage3_Phase6 =
  [Generic, Symptoms, Medications, Exercise, Diet&Fluid, Self-care]
- Duration_Stage3_Phase6_Generic = 3 weeks;
- Schedule_Generic_week1 =
  [1. interactive message, 2. video, 3. video, 4. reinforcement message]

SubPhase is one of [Symptoms, Medications, Exercise, Diet&Fluid in the next 2 lines]
- Schedule_SubPhase_week1 =
  [1. Tip message on benefit 1, 2. Tip message on benefit 2]
- Schedule_SubPhase_week2 =
  [1. Tip message on benefit 3, 2. Tip message on benefit 4]
- Schedule_Self care_week1 = [1. interactive message, 2. quiz,
  3. Tip message on benefit of self-care]
- Schedule_Self care_week2 = [1. quiz, 2. Tip message on benefit of social support]
- Schedule_Self care_week3 = [1. Closing quiz]
- Design Rule1 = no content elements in the weekends;
- Design Rule2 = choose fixed days of week1 and week2 for tip messages;

Output:
1) an example of specification for module/subphase generic

FIG. 12D

COMPUTER-IMPLEMENTED METHOD OF MANUFACTURING A COMPUTER-READABLE STORAGE MEDIUM FOR A REMOTE PATIENT MANAGEMENT SYSTEM

CROSS-REFERENCE TO RELATED APPLICATIONS

This application claims the benefit of U.S. Application Ser. No. 61/287,296, filed Dec. 17, 2009, the contents of which are incorporated herein by reference.

TECHNICAL FIELD

The invention relates to remote patient management systems.

BACKGROUND OF THE INVENTION

The goal of the disease management programs, including remote patient management systems, and lifestyle/behavior change programs such as weight management, smoking cessation, or activity programs is to empower patients to control their complex chronic condition. The key component of these programs is therefore coaching the patient. Coaching addresses the following:

Improving knowledge about the chronic condition or specific aspects of these;

Changing attitudes of the patients toward certain behaviors that they need to adopt in order to adhere to the prescribed medication and lifestyle goals;

Moving a patient through stages of change, e.g., from pre-contemplation, through contemplation, action and maintenance; and Removing perceived barriers and enforcing the benefits that a patient has toward the specific behavior or a goal.

Patient non-compliance decreases the efficacy of pharmacological and non-pharmacological therapy and exposes the patient to clinical destabilization, which can lead to exacerbating disease symptoms. Evidence from clinical trials and validated insights show that the most commonly identified cause of disease worsening, e.g. Heart Failure (HF) decompensation, is non-compliance with medication, low sodium diet, fluid restriction and physical activity. Non-compliance is the precipitating factor of exacerbation, leading to poor clinical outcomes. Therefore, interventions overcoming low patient compliance are needed.

The coaching of patients may be managed with so called remote patient management systems, which are also known as telehealth systems. The coaching of patients may be coded into executable care plans which may be executed by an application hosting device which the patient has access to.

SUMMARY OF THE INVENTION

Care plans may comprise a Coaching Plan (CP). A coaching plan as used herein is the specification or definition of a coaching intervention for execution by a Remote Patient Management (RPM) system. The problem with the current Care Plans is twofold:

Problem 1: The current Remote Patient Management (RPM) systems do not offer methods to the medical professionals to personalize coaching plan by influencing the coaching plan design on a patient base. Care providers have a wealth of clinical experience in addressing patient's chronic conditions, and adapt their face-2-face interactive coaching intervention to the strengths and weaknesses of the individual patients. A remote patient management system provides a selection of guideline-compliant coaching plans, but lacks the ability to easily configure specific coaching plan variants based on local clinical practice and assessment of patient health and behavioral status-dependant determinants of patient compliance to medication therapy and lifestyle changes.

Problem 2: Typically, the care provider can only choose from a predefined set of "static" care plans that have been reviewed and approved to comply with all applicable guidelines and clinical standards. The current coaching plans cannot be dynamically changed, neither for the care provider's local patient population, nor to his personal preferences and convictions, nor to a specific patient's needs nor at run time once they are at the execution phase.

Summing up, none of the existing remote patient management systems are able to generate coaching plans with different specifications per patient covering the patients' variety of determinants of non-compliance as perceived from the medical professional's point of view.

Embodiments of the present invention may address one or more of the aforementioned problems by implementing a computer-implemented method of manufacturing a computer-readable storage medium which can be executed by the remote patient management system. In some embodiments, this method is implemented as a coaching plan configurator. The configurator consists of a coaching plan authoring tool, a coaching plan compiler, and a coaching plan linker—which run in sequence to create a library of executable coaching plans that the remote patient management system can assign to patients, deliver and monitor over time. The linked coaching plan may be integrated into an executable care plan.

The coaching plan authoring tool allows medical professionals or other care providers to define personalized and optimized coaching plans from 1) applicable clinical guidelines, 2) local standards of practice, 3) professional medical judgment of 4) a patient's health and behavioral status and susceptibility to 5) different types of interventions derived from 6) different models of behavior change.

The coaching plan compiler generates the overall coaching plan structure based on internal parameters determined by the coaching plan authoring tool and external parameters like the duration of the intervention as defined by clinical practice, patient needs or preferences, or reimbursement/regulatory boundary conditions. It also creates placeholders for each content element inside this structure, i.e., inside each stage/phase of the intervention The coaching plan linking tool resolves the symbolic names of the placeholder elements that the coaching plan compiler has left in the coaching plan, using content from a content library or multi-media library, and creates an executable care plan, in the format required to "load" by the remote patient management system.

The invention provides for a computer implemented method of manufacturing a computer-readable storage medium containing instructions for execution by a remote patient management system. The computer-readable storage medium as used herein is any storage medium which may be read by a computer or processor. Examples of computer-readable storage medium include but are not limited to: floppy disks, hard disks, solid state hard disk, USB thumb drives, RAM memory, ROM memory, EEPROM memory, and registers in processors or microprocessors. A remote patient management system is a system which may be used to both monitor a patient and also to manage the care of a patient. Remote patient management systems are also known as telehealth systems. The remote patient management system comprises at least one processor for executing the instructions. Execution of the instructions causes the remote patient management system to execute a care plan. A care plan is a day-to-day plan for managing a disease or health condition. The plan starts with setting goals such as taking medications according to predefined regimen, or having 30 min of physical activity at least 5 days per week, or losing weight, or stopping smoking. A care plan may also cover a diet plan for the patient. Care plans may also comprise an exercise plan. Care plans may also comprise schedules for when to take medication. The care plan may also comprise the monitoring of patient vital signs. Patient vital signs are any physical property of the patient which may be measured. Examples of vital signs are weight, blood sugar level, blood pressure, pulse, SpO2, bio-impedance, etc.

The care plan comprises a coaching plan. The coaching plan is a plan for changing the behavior of the patient to facilitate the effectiveness of the therapy during the care plan.

The computer implemented method may comprise providing a computer-readable storage medium. The computer implemented method comprises displaying a list of psychological determinants. When a subject or patient is coached there are a variety of determinants of compliance. For instance there may be a number of patient related determinants such as physiological or psychological factors. Additionally they may also be therapy related, condition related, socioeconomic related, and healthcare system related determinants of compliance. As used herein psychological determinants refers to psychological determinants of compliance. There are different theories and behavioral models which may be used. Different behavioral change models are effective on different groups of people or types of patients. The type of behavioral model to use for coaching also depends upon the style and the beliefs of a particular physician or care giver.

The method further comprises receiving a selection of a group of psychological determinants chosen from a list of psychological determinants. At this stage a list of psychological determinants which a physician or care giver believes is applicable for training the patient is selected. The physician or healthcare provider would choose from this list according to what he or she believes are the biggest factors which determine if the therapy will be successful. The method further comprises generating a list of behavioral models using the group of psychological determinants. Different behavioral models use different approaches towards coaching or educating a patient and therefore are more or less effective on particular psychological determinants Using the list of psychological determinants a list of relevant behavioral models can be constructed.

The method may also comprise displaying the list of behavioral models. The method further comprises receiving a selection of at least one selected behavioral model from the list of behavioral models. The physician or healthcare provider can then choose one or more behavioral models to be used for coaching the patient. The method further comprises determining a timeline for the global structure of the coaching plan using at least the selected behavioral model. The timeline defines the stages of the coaching plan for each of the at least one selected behavioral model. Each stage specifies unresolved symbolic links representing multimedia content, used to coach a patient. Each stage may also specify events which occur during the execution of this stage.

The method further comprises compiling a coaching object file using the timeline. The coaching object file comprises the unresolved symbolic links. The coaching object file at this point may be an executable coaching file; however the symbolic links to the multimedia content have not yet been resolved. It further comprises linking the coaching object file to a library of multimedia content to resolve the unresolved symbolic links. Linking the coaching object file creates the coaching plan. Linking the coaching object file may have several different meanings. For instance it may mean embedding the multimedia content within the care plan; it may also mean moving the library of multimedia content or a portion of the library of multimedia content to the memory of the processor that will execute the coaching plan; it may also mean replacing the unresolved symbolic link by a resolved link to an existing multi-media element. The step may take as input a symbolic generic name for a multi-media content item, for example CHF-Intro-Video, and converts it into a resolved file name such as "_CHF_1_DE_de_v13_640×480_PAL.mp4._" The symbolic generic name may also be converted into a file name with path or even a URL.

The method further comprises integrating the coaching plan into the care plan. At this point the coaching plan is combined into the care plan. The integration of the coaching plan into the care plan depends upon the type of executable instructions used and the type of machine or processor that is used to execute the care plan. The coaching plan and care plan may be combined into a single executable program or the coaching plan may function as a library which is used during the execution of the care plan. The method further comprises writing the care plan to the computer-readable storage medium. The act of writing the care plan to the computer-readable storage medium physically modifies the computer-readable storage medium and transforms it into a component which is able to modify and/or control the operation of the remote patient management system.

In another embodiment the method further comprises the step of receiving physician approval before compiling the coaching plan, whereby the coaching object file becomes a physician approved coaching object file. The method further comprises the step of receiving physician approval of the multimedia content. The coaching plan is physician approved by virtue of the physician approved coaching object file and the physician approved multimedia content. This embodiment is particularly advantageous, because it allows physicians to create a coaching object file which is applicable to a particular group of his or her patients. This plan may then be turned automatically into an approved coaching plan. The coaching plan may be integrated into an approved care plan. In this respect approved care plans may be constructed. The physician approval for the multimedia content and for the coaching object file may be by different physicians. For instance the library of multimedia content may be pre-approved and provided by a service provider for the physician to use with his or her patients.

In another embodiment a behavioral model comprises a set of psychological determinants. This set of psychological determinants are determinants which are addressed by the behavioral model. A behavioral model is selected from the list of behavioral models if the selection of the psychological determinants contains more than a predetermined number of psychological determinants belonging to the group of psychological determinants.

The determination of the timeline comprises using defined rules. Rules about the length and/or content may be used.

In another embodiment the method further comprises receiving a modification to the defined rules.

In another embodiment the defined rules comprise regional regulatory rules.

In another embodiment the defined rules comprise national regulatory rules.

In another embodiment the defined rules comprise rules derived from guidelines authored by professional medical societies.

In another embodiment the defined rules comprise local practice guidelines.

In another embodiment the instructions comprise rules for displaying multimedia content using the measurements by the patient management system as a trigger. The remote patient management system may comprise an application hosting device. The application hosting device may comprise or be connected to a feedback device and the application hosting device may further comprise or be connected to at least one diagnostic medical device. The diagnostic medical devices are for periodically measuring a vital sign of the patient. The measurement of these vital signs may be used to trigger a content element such as a multimedia presentation or a film. For instance, an increased body weight (above certain threshold) of a heart failure patient may trigger an educational segment, a text message, a survey, a quiz, a video clip or an instructional audio clip may be played to coach or educate the patient.

In another embodiment the instructions comprise commands for displaying the contents of each stage. In this embodiment a physician or a healthcare provider or a nurse may see the contents of each stage.

In another embodiment the instructions comprises commands for receiving a modification to the contents of each stage. In this embodiment a physician or healthcare provider may modify the contents of each stage.

In another embodiment the multimedia library comprises charts showing vital sign trends.

In another embodiment the multimedia library comprises educational videos.

In another embodiment the multimedia library comprises quizzes.

In another embodiment the multimedia library comprises surveys.

In another embodiment the multimedia library comprises messages.

In another embodiment the multimedia library comprises tips.

In another embodiment the multimedia library comprises interactive messages.

In another embodiment the multimedia library comprises check lists.

In another embodiment the multimedia library comprises medication check lists.

In another embodiment the multimedia library comprises symptoms check lists.

In another embodiment the multimedia library comprises games. These may be games which educate the patient. They may also be games which provide entertainment but do not perform educating, but are instrumented in determining mental abilities and trends in mental abilities. For example video games may provide a measure of hand eye coordination. These may also be games which are challenging and help to develop mental abilities. For example the game may be a Sudoku game.

In another embodiment the multimedia library comprises games-for-health. Games-for-health are games which engage the patient in health benefiting behavior. For instance a sports type game where the patient engages in physical activity with a controller may be considered a games-for-health.

In another embodiment the multimedia library comprises recipes. Recipes which may be used by the patient and which may promote better eating habits may also be displayed.

In another embodiment the timeline further specifies an introductory stage. The introductory stage is a stage that occurs before all other stages on the timeline. The introductory stage is not specified by one of the at least one selected behavioral models.

In another embodiment the step of compiling the coaching object file comprises using a set of constraints which limit the iteration of the coaching plan.

In another embodiment the method further comprises the step of receiving a list of psychological determinants.

In another embodiment the method further comprises receiving a group of behavioral models.

In another embodiment the list of behavioral models is chosen from the group of behavioral models.

In another embodiment each of the group of behavioral models comprises a definition of what psychological determinants it addresses.

In another embodiment the method further comprises the step of receiving a library of multimedia content.

In another embodiment the library of multimedia content comprises multimedia elements. Each multimedia element comprises a reference to which of the group of behavioral models it addresses. Each multimedia element comprises a reference to which of the list of psychological determinants it addresses.

In another embodiment the behavioral model defines events in a stage of the coaching plan which are chosen using a behavioral modification model.

In another embodiment the remote patient management system comprises an application hosting device. The hosting device comprises or may be connected to at least one diagnostic medical device.

In another embodiment the diagnostic medical device is a blood pressure monitor. The blood pressure monitor may be for instance a blood pressure cuff that monitors the blood pressure of the patient.

In another embodiment the diagnostic medical device is a heart rate monitor.

In another embodiment the diagnostic medical device is a scale for monitoring body weight of the patient.

In another embodiment the diagnostic medical device is a blood sugar monitor.

In another embodiment the diagnostic medical device is a thermometer for monitoring body temperature. The thermometer may be able to communicate with the computing device or the patient may input the temperature into the patient user interface.

In another embodiment the diagnostic medical device is a pedometer for monitoring patient activity.

In another embodiment the diagnostic medical device is a body fat analyzer.

In another embodiment the diagnostic medical device is a cholesterol monitor.

In another embodiment the diagnostic medical device is a urine test strip analyzer. A urine test strip analyzer is defined herein as a device which uses urine test strips or other chemical means to analyze urine. For instance a urine test strip analyzer can be used to detect metabolites which are generated by the use of illegal or addictive drugs.

In another embodiment the diagnostic medical device comprises an interface or screen on the patient user interface which is adapted for receiving a numerical pain ranking from the patient. A numerical pain ranking is a numerical value which is assigned by the patient which is used to describe the pain that a patient is currently experiencing. For instance a value of 0 could indicate that the patient experiences no pain and a value of 10 could indicate that the patient experiences excruciating pain which cannot be withstood.

In another embodiment the diagnostic medical device is a breath alcohol device for determining blood alcohol content. The breath alcohol device could be used to monitor consumption of alcohol by an alcoholic.

In another embodiment the diagnostic medical device is a saliva analyzer. The saliva analyzer may be adapted for detecting the use of specific drugs. For instance the detection of illegal or addictive drugs.

In another embodiment the diagnostic medical device is a bioimpedance sensor for determining the level of fluid in the body.

In another embodiment the instructions comprise rules that trigger an element of the library of multimedia content when a scheduled measurement of a vital sign by the at least one vital diagnostic medical device is not received. For instance if a diabetic fails to perform a blood sugar measurement a reminder or an educational multimedia clip may be played on the importance of simply measuring the blood sugar when one has diabetes.

In another embodiment the instructions comprise rules that trigger an element of the library of multimedia.

In another embodiment the instructions comprise rules that trigger an element of the library of multimedia on a measurement of a vital sign when at least one vital sign measured by a diagnostic medical device is outside of a predetermined range. For instance if a patient has a higher than normal blood sugar reading the patient may receive a reminder or may be instructed to view a film about the importance of not eating too much sugar when one has diabetes.

In another aspect the invention provides for a first computer-readable storage medium containing instructions that when executed by a processor of a computing device cause the computing device to perform a method of manufacturing a second computer-readable storage medium containing instructions for execution by a remote patient management system. The remote patient management system comprises at least one processor for executing the instructions. Execution of the instructions causes the remote patient management system to execute a coaching plan.

The method may comprise providing the second computer-readable storage medium. In some embodiments the first and second computer-readable storage mediums may be the same computer-readable storage medium. The method comprises displaying a list of psychological determinants. The method further comprises receiving a selection of a group of psychological determinants chosen from the list of psychological determinants. The method further comprises generating a list of behavioral models using the group of psychological determinants. The method further comprises receiving a selection of at least one selected behavioral model from the list of behavioral models. In some embodiments the method further comprises displaying the list of behavioral models before receiving the selection of at least one selected behavioral model from the list of behavioral models.

The method further comprises determining a timeline for the global structure of the coaching plan using the at least one selected behavioral model. The timeline defines the stage of the coaching plan for each of the at least one selected behavioral models. Each stage specifies unresolved symbolic links representing multimedia content. The method further comprises compiling a coaching object file using the timeline. The coaching object file comprises the unresolved symbolic links.

The method further comprises linking the coaching object file to a library of multimedia content to resolve the unresolved symbolic links. Linking the coaching object file creates the coaching plan. The method further comprises integrating the coaching plan into the care plan. The method further comprises writing the care plan to the second computer-readable storage medium.

In another embodiment the instructions on the first computer-readable storage medium contain instructions for implementing the method using a wizard displayed on a graphical user interface. A wizard is a set of executable instructions which gather information from a user using graphical user interfaces. Information gathered by the wizard is then used to perform some sort of optimization or configuration.

In another aspect the invention provides a method for a remote patient management system. The remote patient management system comprises an application hosting device among others. The application hosting device comprises or is connected to a feedback device. The application hosting device further comprises or is connected to at least one diagnostic medical device. The feedback device provides a user interface which allows the patient to enter data or make a selection. A diagnostic medical device is a measuring device which is used to measure a vital sign of a patient. A vital sign is any measurable property of a patient. For instance the weight or the blood sugar are two examples.

The remote patient management system further comprises a healthcare provider interface. This is an interface which a doctor or other healthcare provider may use to interact with the remote patient management system. The healthcare provider interface may be a display and keyboard on a computer which is part of the patient management system or it may be a computer that is networked or connected to other components of the remote patient management system. The remote patient management system comprises a computing device comprising at least one processor. The remote patient management system further comprises a first computer-readable storage medium containing instructions that when executed by the at least one processor cause the computing device to perform a method of manufacturing a second computer-readable storage medium containing instructions for execution by a remote patient management system.

The remote patient management system comprises at least one processor for executing the instructions. Execution of the instructions causes the remote patient management system to execute a coaching plan that comprises displaying a list of psychological determinants. The method further comprises receiving a selection of a group of psychological determinants chosen from the list of psychological determinants. The method further comprises generating a list of behavioral models using the group of psychological determinants.

The method further comprises receiving a selection of at least one selected behavioral model from the list of behavioral models. The method further comprises determining a timeline for the global structure of the coaching plan using the at least one selected behavioral model. The timeline defines stages of the coaching plan for each of the at least one selected behavioral models. Each stage specifies unresolved symbolic links representing multimedia content.

The method further comprises compiling a coaching object file using the timeline. The coaching object file comprises the unresolved symbolic links. The method further comprises linking the coaching object file to a library of multimedia content to resolve the unresolved symbolic links. Linking the coaching object file creates the coaching plan. The method further comprises integrating the coaching plan into the care plan. The method further comprises writing the care plan into the computer-readable storage medium. For this remote patient management system and also for the previously mentioned computer implemented method and computer-readable storage medium the first computer-readable storage medium may also be the second computer-readable storage medium. For instance the instructions of the first computer-readable storage medium and the instructions of the second computer-readable storage medium may both be stored on the same hard drive or may also be in the computer's memory.

In another embodiment the application hosting device comprises at least one processor. The second computer-readable storage medium is executed by the application hosting device.

BRIEF DESCRIPTION OF THE DRAWINGS

In the following preferred embodiments of the invention will be described, by way of example only, and with reference to the drawings in which:

FIG. 5 shows a table which illustrates default values of input parameters or stages of a coaching plan specified by different behavioral change models;

FIG. 8 illustrates the receiving a selection of determinants and behavioral models during the computer implemented method of FIG. 7;

FIGS. 11A-1 and 11A-2 together form a table which illustrates how the global structure of the stages and the phases of the stages are designed during the computer implemented method of FIG. 7;

FIGS. 11B-1 and 11B-2 together form a table that is a continuation of the table of FIGS. 11A-1 and 11A-2;

FIGS. 11C-1 and 11C-2 together form a table that is a continuation of the table of FIGS. 11A-1, 11A-2, 11B-1, and 11B-2;

FIG. 12A is a table which illustrates in detail duration and rules for distributing content elements during the computer implemented method of FIG. 7;

FIG. 12C is a continuation of the table of FIG. 12A and 12B;

FIG. 12D is a continuation of the table of FIG. 12A, 12B, and 12C; and

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
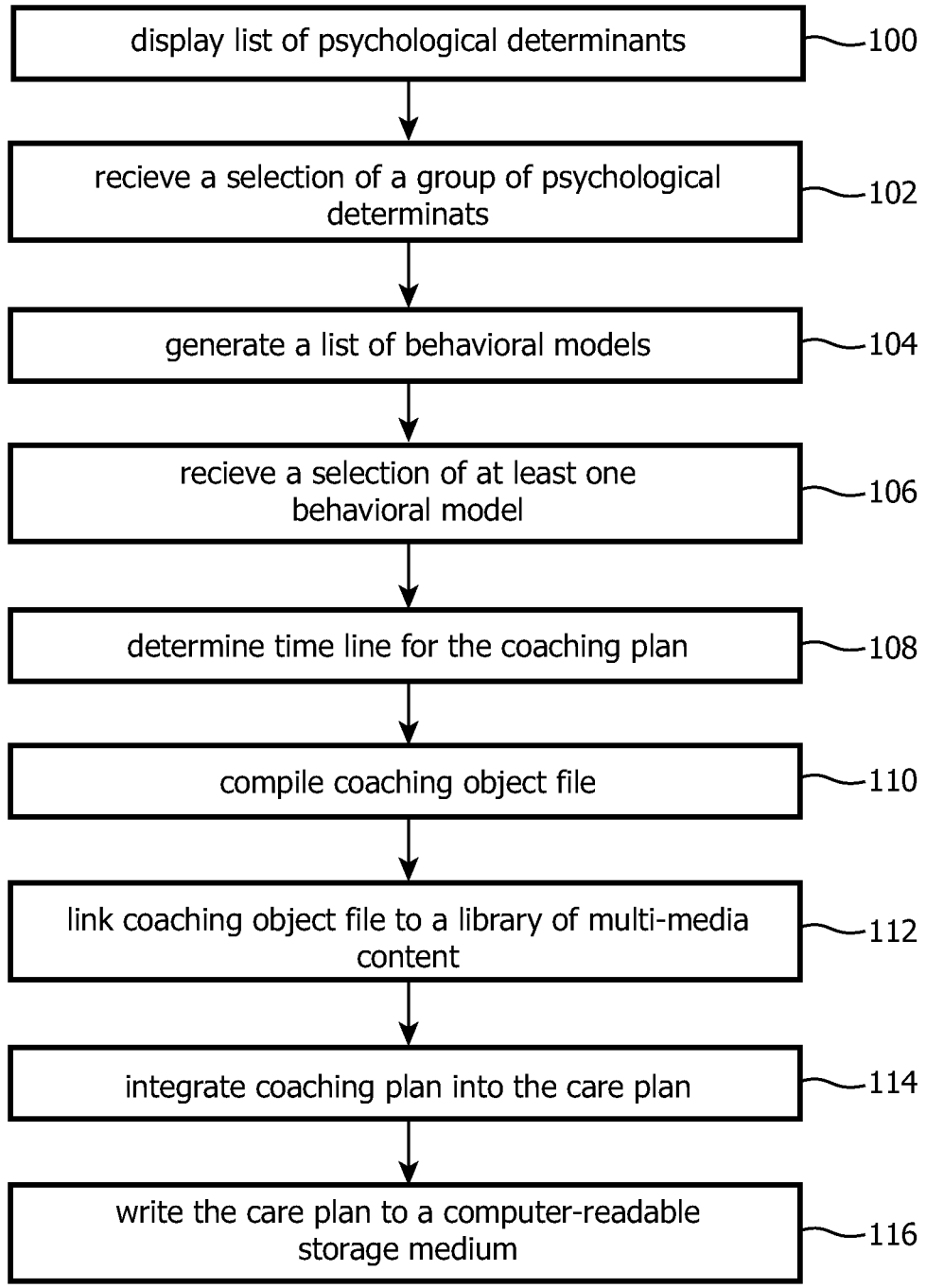
FIG. 1 shows a block diagram which illustrates a method according to an embodiment of the invention.

FIG. 1 shows a block diagram which illustrates a method according to an embodiment of the invention. In step 100 a list of psychological determinants is displayed. In step 102 a selection of a group of psychological determinants chosen from the displayed list of psychological determinants is received. In step 104 a list of behavioral models is generated using the selected group of psychological determinants. The list of behavioral models may contain a description of which psychological determinants that behavioral model affects. In step 106 a selection of at least one behavioral model is received. In step 104 a timeline for the coaching plan is determined In step 110 a coaching object file is compiled using events contained within the timeline. In step 112 the coaching object file is linked to a library of multimedia content. The link may be explicit and the multimedia content may be embedded in the resulting care plan or the link may be turned into a specific address for multimedia content which is either stored locally or remotely. In step 114 the coaching plan is integrated into the care plan. In step 116 the care plan is written to a computer-readable storage medium.

Figure 2:
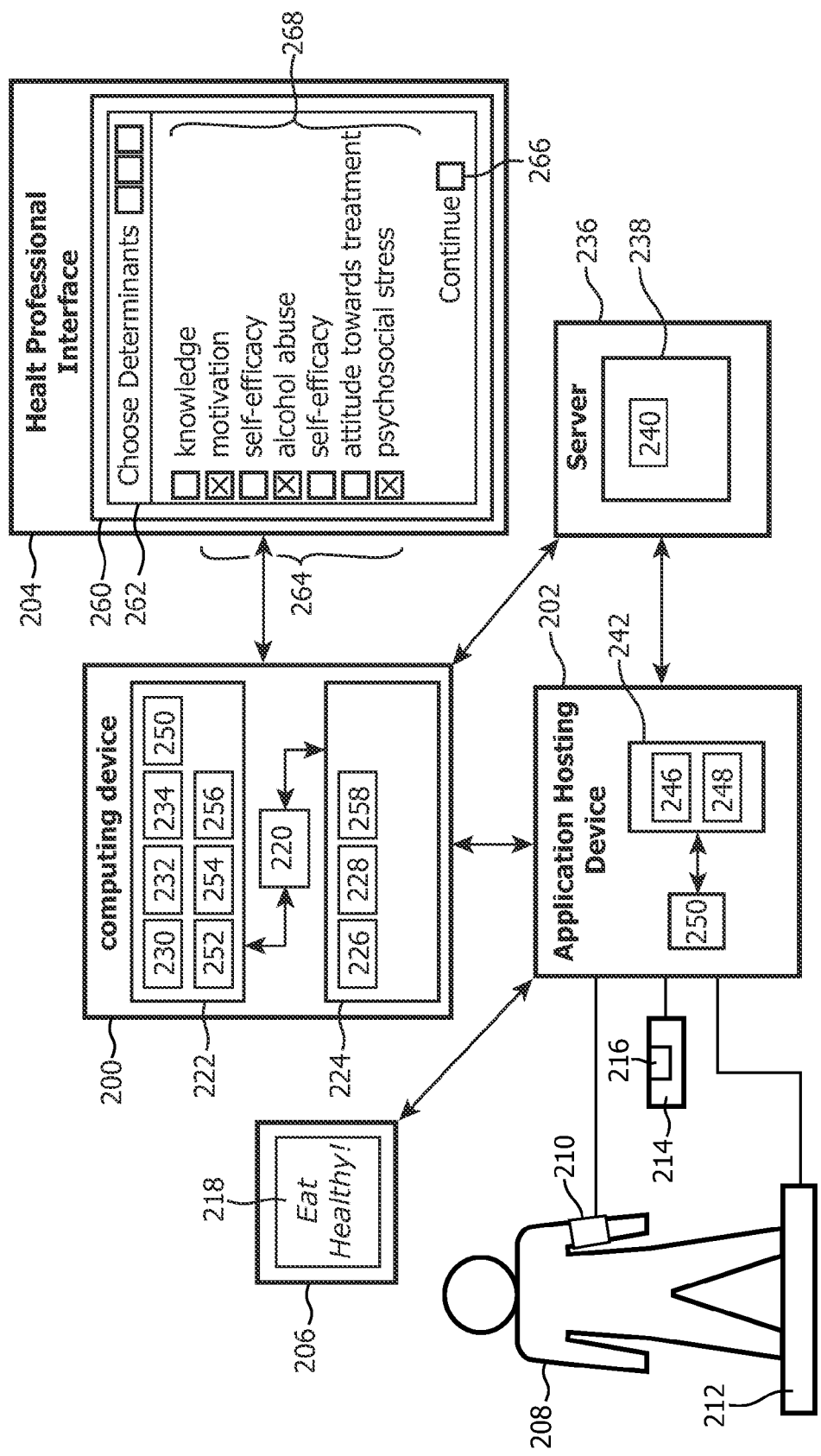
FIG. 2 shows a functional block diagram of a remote patient management system according to an embodiment of the invention.

FIG. 2 shows a functional block diagram of a remote patient management system. The remote patient management system comprises a computing device 200. The computing device 200 is able to communicate with an application hosting device 202. The application hosting device is typically located at the home of a patient 208. The computing device 200 is also connected to a health professional interface 204. The health professional interface may be a computer networked to the computing device 200. The health professional interface 204 may also be a portable or handheld computing device. The health professional interface 204 may also be provided as a web service available over the internet.

The application hosting device 202 is connected to a user interface 206 and/or feedback device. The user interface is adapted for displaying information and/or multimedia to the patient 208. The application hosting device 202 may be adapted for connecting to one or more diagnostic medical devices 210, 212, 214. For instance the patient 208 is shown with a blood pressure cuff 210 which is able to communicate with the application hosting device 202. The subject 208 is also shown standing on a scale 212 which relays the weight measurement of the patient 208 to the application hosting device 202. There is also a urine test strip reader 214 which is adapted for receiving a urine sample 216. Urine test strip readers use paper or other chemical means to measure a chemical property of urine 216. Since a urine test strip reader may be used for detecting the use of illegal drugs. All three of these diagnostic medical devices are connected to the application hosting device 202 such that data may be automatically acquired by the application hosting device 202. The user interface 206 may also comprise a display 218 which is able to display messages and/or multimedia.

The computing device 200 may be one or more computing devices. The computing device 200 in this embodiment is shown as having a processor 220. The processor 220 is connected to computer storage 222 and to computer memory 224. The computer memory 224 is shown as containing instructions 226. The instructions 226 contain a set of instructions for performing an embodiment of the method according to the invention. Also shown within the computer memory 224 is a care plan 228. The instructions for performing the method are also shown as being stored in the computer storage 222. Block 230 represents instructions for performing an embodiment of the method according to the invention. Block 232 is also within the computer storage 222 and represents a care plan stored on the computer storage 222. Also within the storage 222 is a multimedia library 234. The multimedia library may be stored in various locations. For instance also shown in this diagram is a server 236. The server 236 may or may not be part of the remote patient management system. The server 236 comprises computer storage 238. Located within the computer storage 238 is another multimedia library 240.

The application hosting device 202 also has computer memory 242. Located within the computer memory 242 is a care plan 246. Also located within the computer memory 242 is a multimedia library 248. The application hosting device may use the local multimedia library 248 or it may also access the multimedia library 234 or the multimedia library 240. Not shown in this FIG. but the application hosting device may also have computer storage. The care plan and/or the multimedia library may also be located on this computer storage. The application hosting device also comprises a processor 250 for executing the instructions contained within the care plan 246. Also located within the computer storage 222 is a library of care plan executables 250. These executables 250 may be used by the instructions for performing the method 226 for the integration of the coaching plan into a finished coaching plan 228. The computer storage 222 further comprises a regulatory guidelines database 252. The computer storage 222 further comprises a behavioral models database 254. This database 254 contains the behavioral models used for generating the list of behavioral models. The computer storage 222 further comprises a determinants of compliance database. This database 256 contains the psychological determinants used for displaying the list of psychological determinants.

Within the computer memory 224 may also be stored the intermediate coaching plan 258. The health professional interface 204 may comprise a display 260. Displayed within the display 260 is a graphical user interface 262 of a wizard which is used for implementing an embodiment of the method. The wizard 262 has a group of check boxes which allow a physician or a care provider to select determinants. There is a continue button 266 that the physician or care provider may press after the psychological determinants have been selected. Adjacent to the check boxes 264 is a list of psychological determinants 268.

Figures 3, 4:
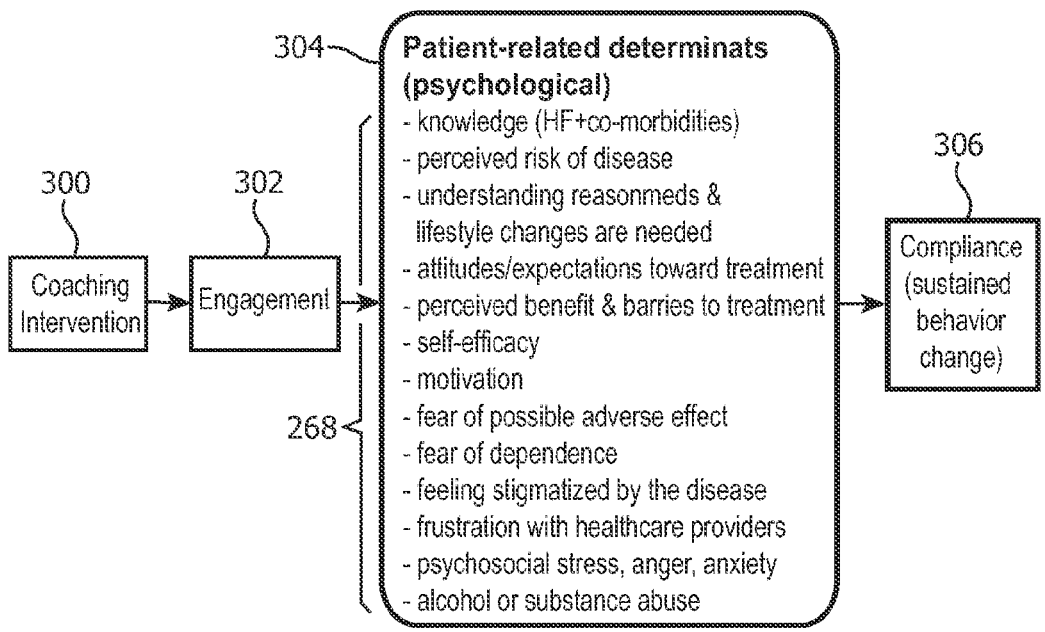
FIG. 3 illustrates the association between a coaching intervention and compliance mediated by patient engagement and the determinants of compliance.
FIG. 4 shows a table which illustrates examples of behavioral models addressing specific psychological determinants.

FIG. 3 illustrates an association between a coaching intervention and compliance mediated by patient engagement and the determinants of compliance. Step 300 is a coaching intervention. The coaching intervention 300 leads to compliance 306 which is a sustained behavior change in the patient. The compliance 306 is achieved by first engaging 302 the patient. Once engagement 302 has been achieved there are a number of determinants of compliance. Block 304 represents psychological determinants of compliance. Within block 304 is a list 268 of possible psychological determinants that may effect a patient's compliance 306.

FIG. 4 shows a table of examples of behavioral models addressing specific psychological determinants. In column 400 four different behavioral change models are listed. In column 402 psychological determinants that are associated with that particular model are listed. During operation of the system a physician or healthcare provider is presented with a list of psychological determinants. By matching these selected psychological determinants to the determinants in column 402 behavioral change models 400 which may be appropriate can be selected.

FIG. 5 shows a table which illustrates default values of input parameters perstages of a coaching plan specified by different behavioral change models. Row 500 lists four different behavioral change models that are illustrated in this table. The values in column 502 pertain to the health belief model. The entries in column 504 pertain to the entertainment education behavioral change model. The entries in column 506 pertain to the theory of planned behavior behavioral change model. And the items in column 508 pertain to the self-regulation behavioral change model. Row 510 indicates the duration of a particular stage in weeks. Row 512 specifies the number of phases for each of these stages. A phase is a sub-unit of a stage. Row 514 indicates the names of the various phases. The name of each phase starts with a capital letter. For example in column 502 there are three phases for this stage. Their names are Perceived severity, Perceived benefits, and Perceived barriers.

Row 516 indicates rules which may be applied to determine when a goal of a particular stage has been achieved. For instance in column 508 a next stage rule that is listed is goal setting is equal to true. This would indicate that the patient understands how to properly set goals. The rows indicated by numeral 518 indicate types of content elements which may be used by a particular behavioral change model. For example the entertainment education 504 behavioral change model specifies that videos and quizzes are used. The self-regulation 508 behavioral change model specifies that messages and quizzes are used. Row 520 indicates how many days per week content elements are distributed to the patient. For the entertainment education 504 behavioral change model content is distributed three days per week. For the self-regulation 508 behavioral change model content elements are distributed to the patient four times per week.

In row 522 the maximum number of content elements that are distributed to the patient per day is specified. The rows specified by numeral 524 indicate possible design rules for the design of the stages. For example a video teaching quiz should be sent at least one day later than the corresponding video. This rule is useful because if the content is tested at least one day after the video it is a better measure of patient's retention of the information in the video than if the quiz is taken immediately afterwards.

Figure 6:
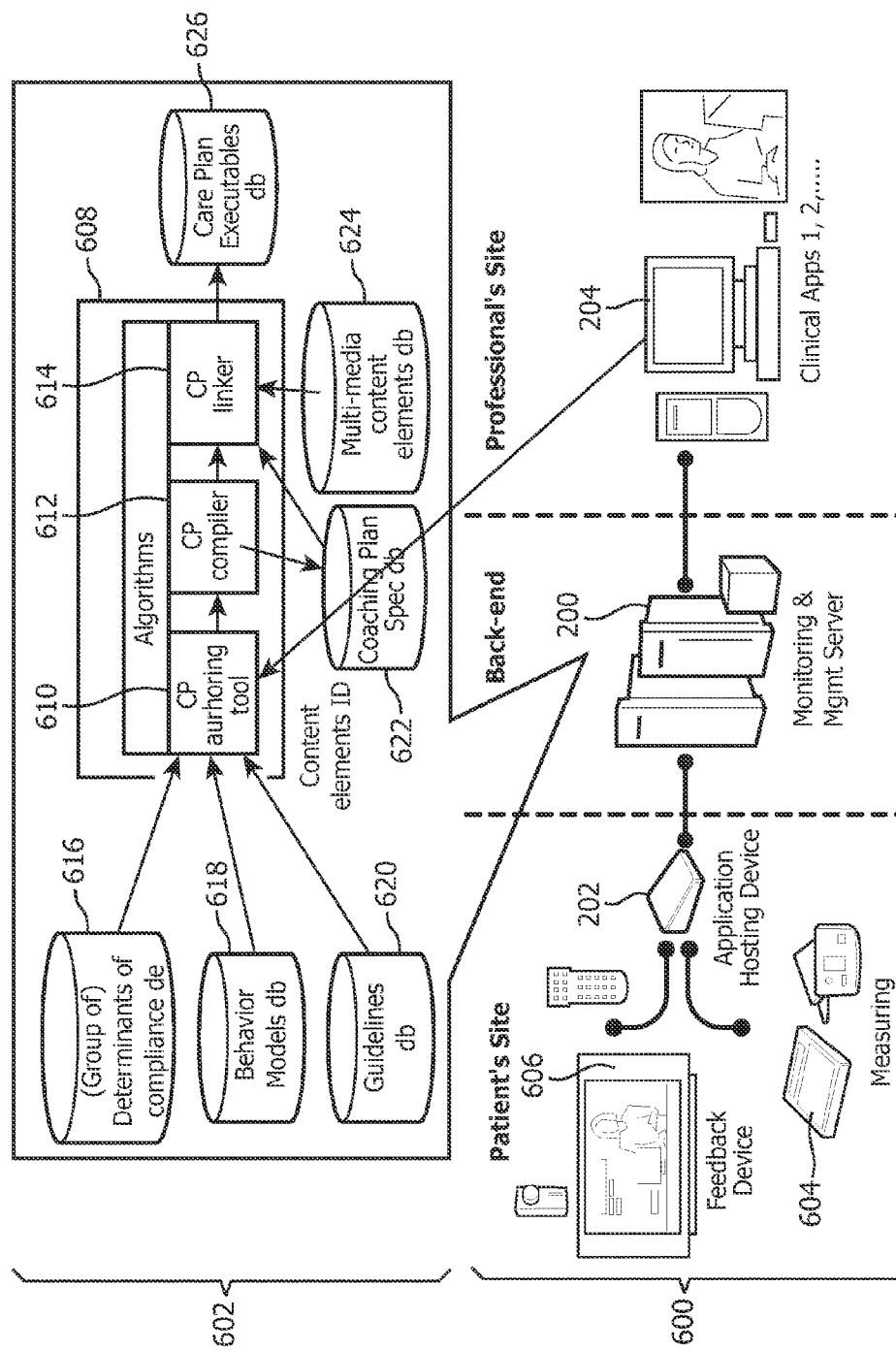
FIG. 6 shows a functional block diagram of a remote patient management system according to a further embodiment of the invention.

FIG. 6 illustrates a remote patient management system according to an embodiment of the invention. This FIG. illustrates two aspects of the remote patient management system. The lower half 600 illustrates the physical components of the remote patient management system. The top part 602 illustrates a possible implementation of software for performing the computer implemented method or the organization of a computer-readable storage medium for implementing that method. The hardware component 600 comprises a patient site, a back end, and a professional site. The patient site comprises an application hosting device 202. The application hosting device is connected to one or more diagnostic medical devices 604. The application hosting device is also connected to a feedback device 606. The feedback device may comprise devices for displaying and receiving information from the patient. For instance the feedback device may comprise a computer, a web interface, a television with a controller for providing feedback and a camera which allows a healthcare provider to observe the patient.

Application hosting device 202 is connected to a computing device 200. In this embodiment the computing device 200 is shown as being one or more servers which are used for monitoring and managing the remote patient management system. The computing device 200 is also connected to a health professional interface. As mentioned before the health professional interface may be a computer or it may be a terminal or web interface which connects to the monitoring and management server 200. In some embodiments the computing device 200 and the health professional interface 204 may be combined into the same system. In the functional organization 602 of the software components there is a collection of computer implementable instructions 608 which may be used for performing an embodiment of the computer implemented method according to the invention. The computer implementable instructions 608 comprise instructions and algorithms for implementing a coaching plan authoring tool 610, a coaching plan compiler 612, and a coaching plan linker 614.

The coaching plan authoring tool 610 comprises instructions for gathering information from the health professional interface 204. For instance the coaching plan authoring tool 610 may be responsible for performing instructions for displaying a list of psychological determinants, receiving a selection of a group of psychological determinants chosen from the list of psychological determinants, generating a list of behavioral models using the group of psychological determinants, receiving a selection of at least one selected behavioral model from the list of behavioral models, and determining a timeline for the global structure of the coaching plan using the at least one selected behavioral model.

Once this has been completed the coaching plan authoring tool 610 instructions of the coaching plan compiler 612 are executed. Instructions of the plan compiler 612 may comprise compiling a coaching object file using the timeline. The coaching object file comprises unresolved symbolic links which represent multimedia content. After the instructions of the coaching plan compiler 612 are completed the instructions of the coaching plan linker 614 may be executed. The coaching plan linker may link the coaching object file to a library of multimedia content to resolve the unresolved symbolic links. The coaching plan linker may also integrate the coaching plan into the care plan. Computer implemented instructions may also comprise instructions for writing the care plan to a computer-readable storage medium.

The software components 602 of the remote patient management system further comprise a database 616 containing determinants of compliance, a database of behavioral models 618, and a database of guidelines 620 which are all accessible to the coaching plan authoring tool 610. The coaching plan compiler is able to write compiled coaching plans to a coaching plan database 622. These coaching plans in the coaching plan database 622 may be stored for later use. The coaching plan linker 614 is able to access the coaching plan database 622 and also a library 624 of multimedia content. The coaching plan linker 614 is then able to write care plan executables into a database 626.

Traditionally, a program language compiler translates programs written in high-level language to assembly languages. In analogue, the coaching plan compiler proposed in this ID translates coaching plans defined in the medical professionals language to formalized specification in terms of type of content elements and their schedule.

A possible implementation of the coaching plan compiler, in pseudo code, is:

```
Create specification_stage of duration_stage
Create content_slots by
    day =1
    while (day < duration_stage)
        create content_slot
        assign CoEl by looping through content_schedule
        day += content_distribution
    end
```

Figure 7:
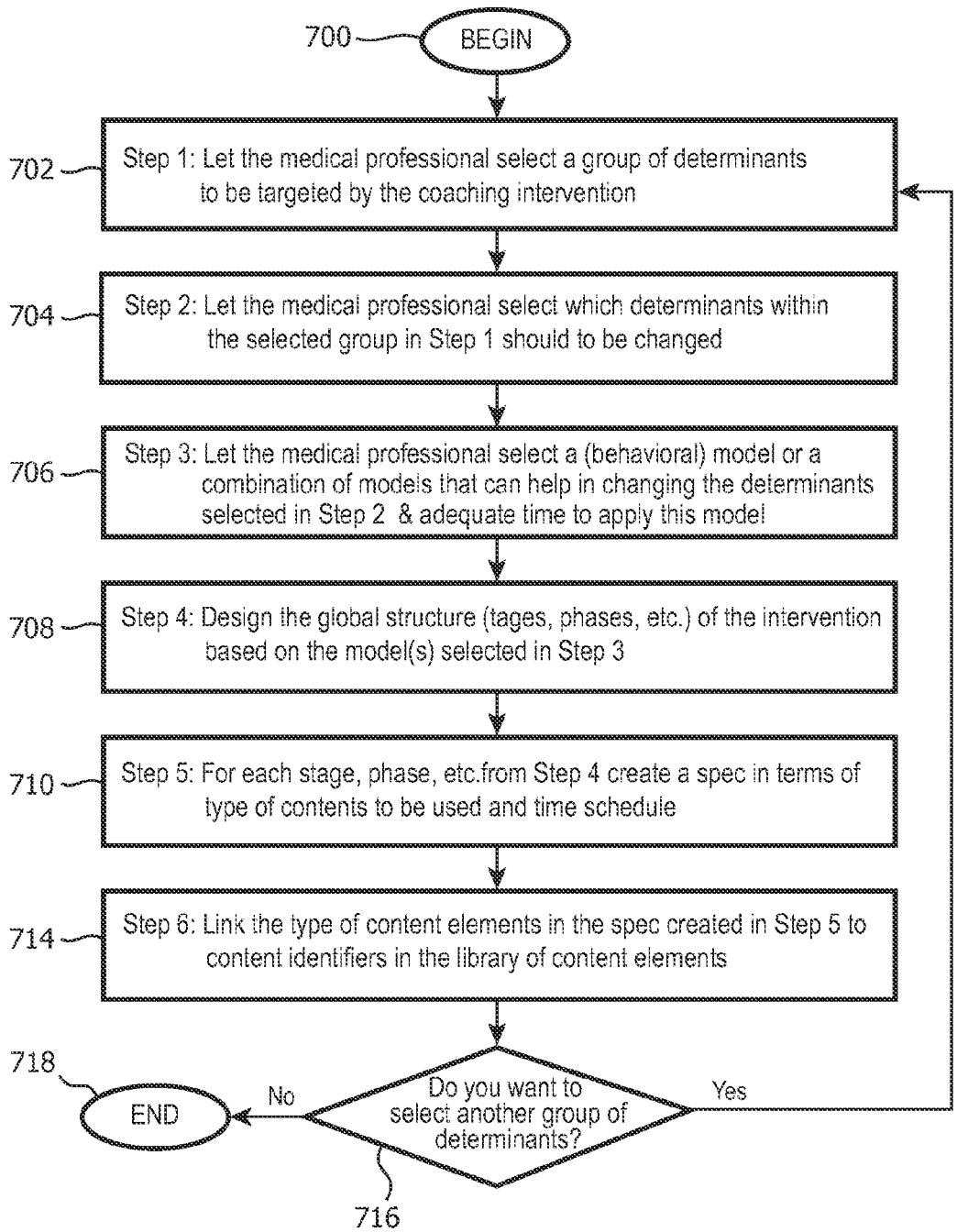
FIG. 7 illustrates an embodiment of a computer implemented method according to an embodiment of the invention.

FIG. 7 illustrates a possible embodiment of a computer implemented method according to an embodiment of the invention. In step 700 the method is begun. In step 1 the medical professional selects a group of determinants to be targeted by the coaching intervention. In the computer implemented method the group of determinants to be targeted is received from the medical professional. In step 704 the medical professional selects which determinants within the selected group in step 702 should be changed. The selected determinants are received from the medical professional. In step 706 the medical professional selects a behavioral model or a combination of models that can help in changing the determinants selected in step 704 and adequate time is allocated to apply this model or models.

In step 708 the global structure which includes stages, phases and sub-components of phases of the intervention is based upon the models selected in step 706. There is a stage that corresponds to each of the behavioral modification models. Phases are sub-structures of stages. In step 710, each stage and phase from step 708 are specified in terms of the type of content elements to be used and the time schedule.

In step 714 the type of content elements are linked to the specification created in step 710 to content identifiers in a library and/or multimedia. In step 716 the healthcare provider is allowed to select if he or she would like to select another group of determinants. If the physician selects yes then the method is performed again starting at step 702. If the healthcare provider does not want to then the method ends 718.

Embodiments of the invention may offer the possibility to the medical professionals (e.g. a heart failure nurse, or a cardiologist, or a general practitioner) to select per patient:
1) the group of determinants to be targeted by the coaching intervention;
2) which determinants within the selected group have to be changed; and
3) the (behavioral) model or a combination of models that can help in changing the selected determinants.

These three points are Steps 702, 704, and 706 of the algorithm illustrated in FIG. 7. The choices made in Steps 702, 704, and 706 are based on the knowledge and experience a medical professional has with respect to a particular patient plus guidelines based recommendations. The coaching plan Authoring Tool allows the medical professionals to create a personalized coaching plan based on the individual approach they have to a patient, starting from an approved structure derived from clinically proven behavior models/theories, and ensuring that the output is conform to local clinical protocols. The tool takes into account the medical professional's preferences with respect to preferred treatment, specific cultural differences and well established local protocols.

Having the input of the medical professional at Steps 702, 704, and 706, the coaching plan compiler performs Steps 708 and 710 of the algorithm illustrated in FIG. 7 to translate this input into:

4) an intervention structure in terms of stages and phases based on the selected behavioral model(s) and the intervention strategies that the model offers.
5) a specification for each stage/phase in terms of type of content elements to be used and time schedule.

Both Steps 708 and 710 have a number of input parameters (e.g. stages of the coaching interventions, phases per stage, total duration of the coaching intervention, duration of each stage/phase, etc.) listed in the table of FIG. 5 and elaborate in the embodiment. These parameters allow for personalization of the coaching plan per patient. They have default values as indicated in the table of FIG. 5 that can be overruled by:

an external source, e.g. total duration of the coaching intervention=duration of a reimbursed intervention, duration required by patient status, duration of a clinical trial;

a patient assessment, which is done either by the remote patient management system or the medical professional, e.g. duration of Stage 1 for Patient A=12 weeks whilst duration of Stage 1 for Patient B=6 weeks;

Finally, the coaching plan linker performs Step 714 of the algorithm illustrated in FIG. 7:

6) a link between the type of content elements in each specification created in Step 710 to content identifiers in the library of content elements.

The coaching plan configurator algorithm illustrated in FIG. 7 can be run several times with different selection of either (group of) determinants of compliance or/and behavioral models in (Step 702) Steps 704 and 706, respectively. This will result in a set of coaching plan forming a repository of coaching plan specs. Hence, the output of the coaching plan configurator is a repository of coaching plan specifications (specs) of a coaching intervention provided to a patient by the telehealth system and endorsed by a medical professional, e.g. a cardiologist, a heart failure nurse, or a general practitioner. The coaching plan configurator can offer the medical professionals the possibility to sign off a coaching plan, i.e. approving it for execution.

FIG. 8 shows a table which illustrates steps 702, 704 and 706 from FIG. 7 in greater detail. The rows of this table 702, 704 and 706 correspond to these three steps of FIG. 7. Column 800 shows the input for each of the steps 702, 704 and 706. Column 802 shows the output for each of these steps 702, 704 and 706. For step 702 the input is a group of determinants. For the output the medical professional selects a group of determinants for a particular patient. For example the patient related group of determinants and in particular the psychological determinants are selected. For step 704 for the input 800 a list of psychological determinants is displayed. For the output 802 the medical professional selects a number of determinants to be addressed. For example the physician may select knowledge and self-efficacy. In step 706 the input is a list of behavioral models that can modify the selected determinants. In step 706 the output 802 is the selection by a medical professional of a combination of models to address these selected determinants For example if knowledge and self-efficacy is best addressed by the entertainment education and self-regulation theory models.

Figure 9:
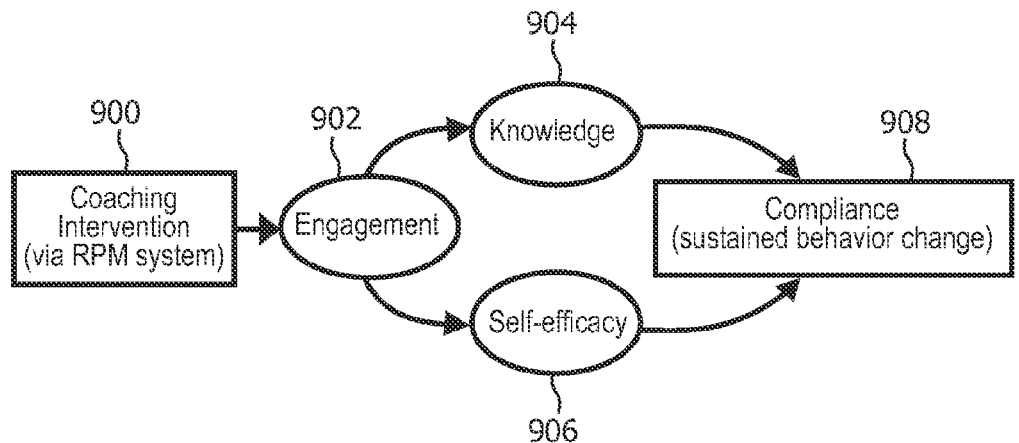
FIG. 9 illustrates how two selected patient-related determinants may be addressed during the coaching plan.

FIG. 9 shows two patient-related determinants have been selected to be influenced during the coaching plan. In step 900 the coaching intervention via a remote patient management system is initiated. Through the use of the remote patient management system the patient is engaged 902 in the coaching plan. Through the following of the coaching plan the knowledge 904 of the patient and the self-efficacy 906 of the patient is increased. This increase in the knowledge 904 and the self-efficacy 906 leads to compliance 908 which is a sustained behavior change in the patient.

Figure 10:
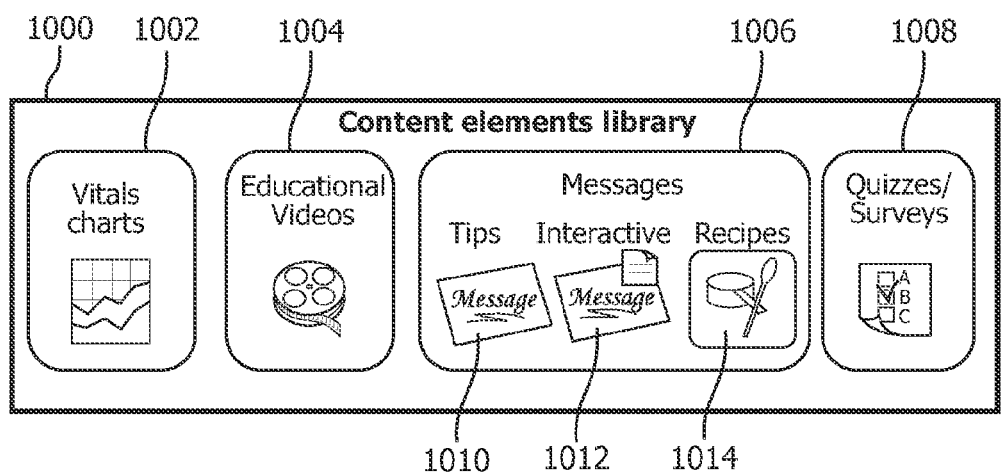
FIG. 10 illustrates the contents of a library of multimedia content.
Figures 1, 11A:
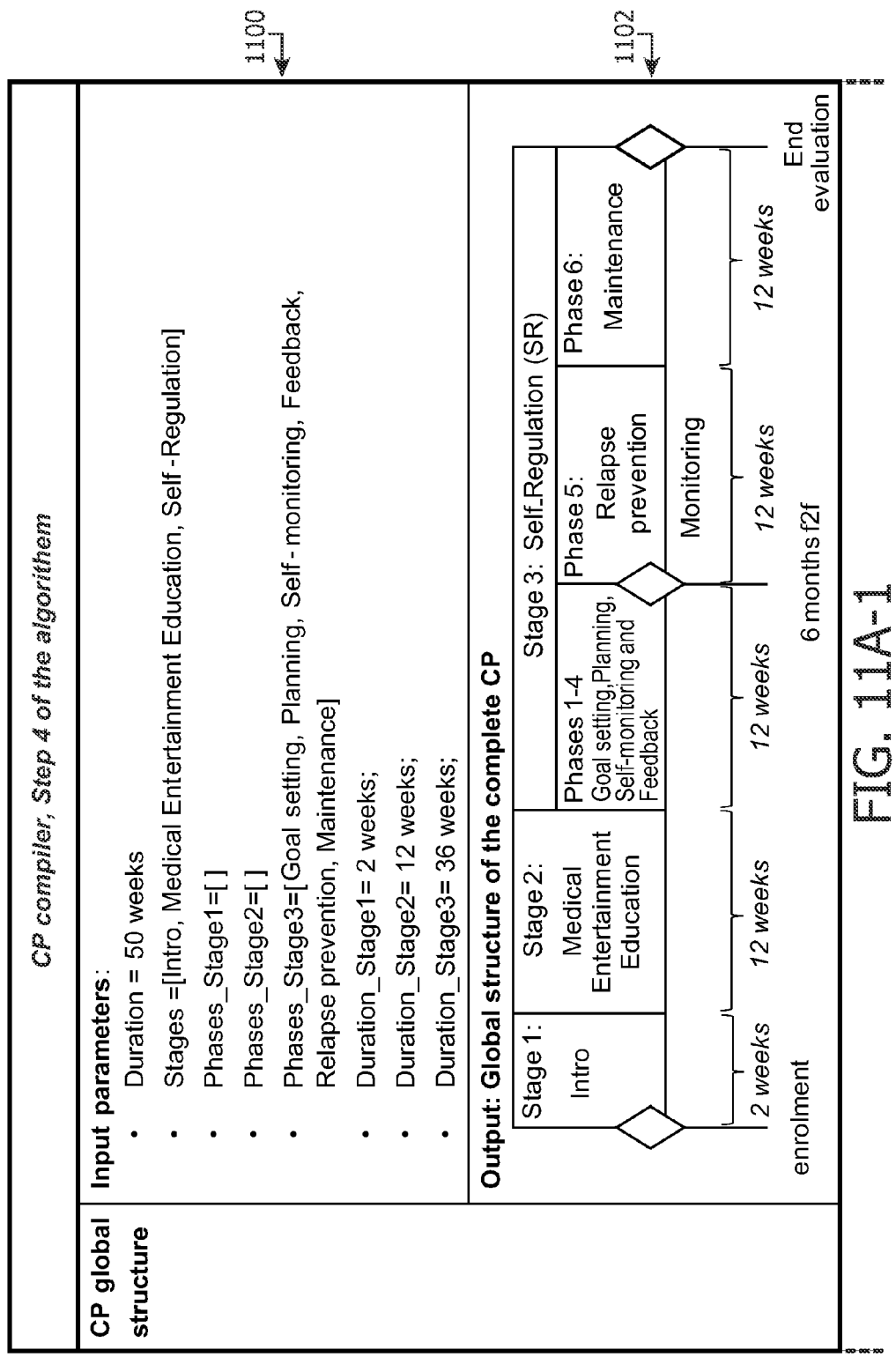
Figures 2, 11A:
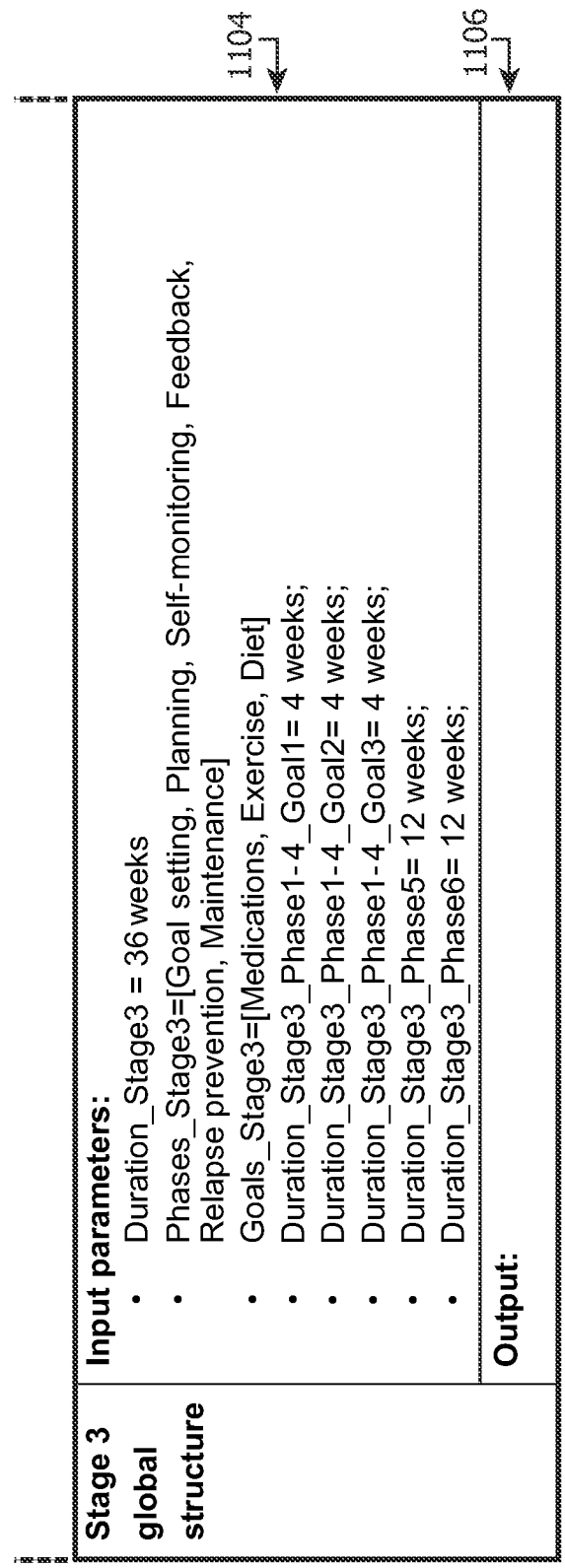
Figures 2, 11B:
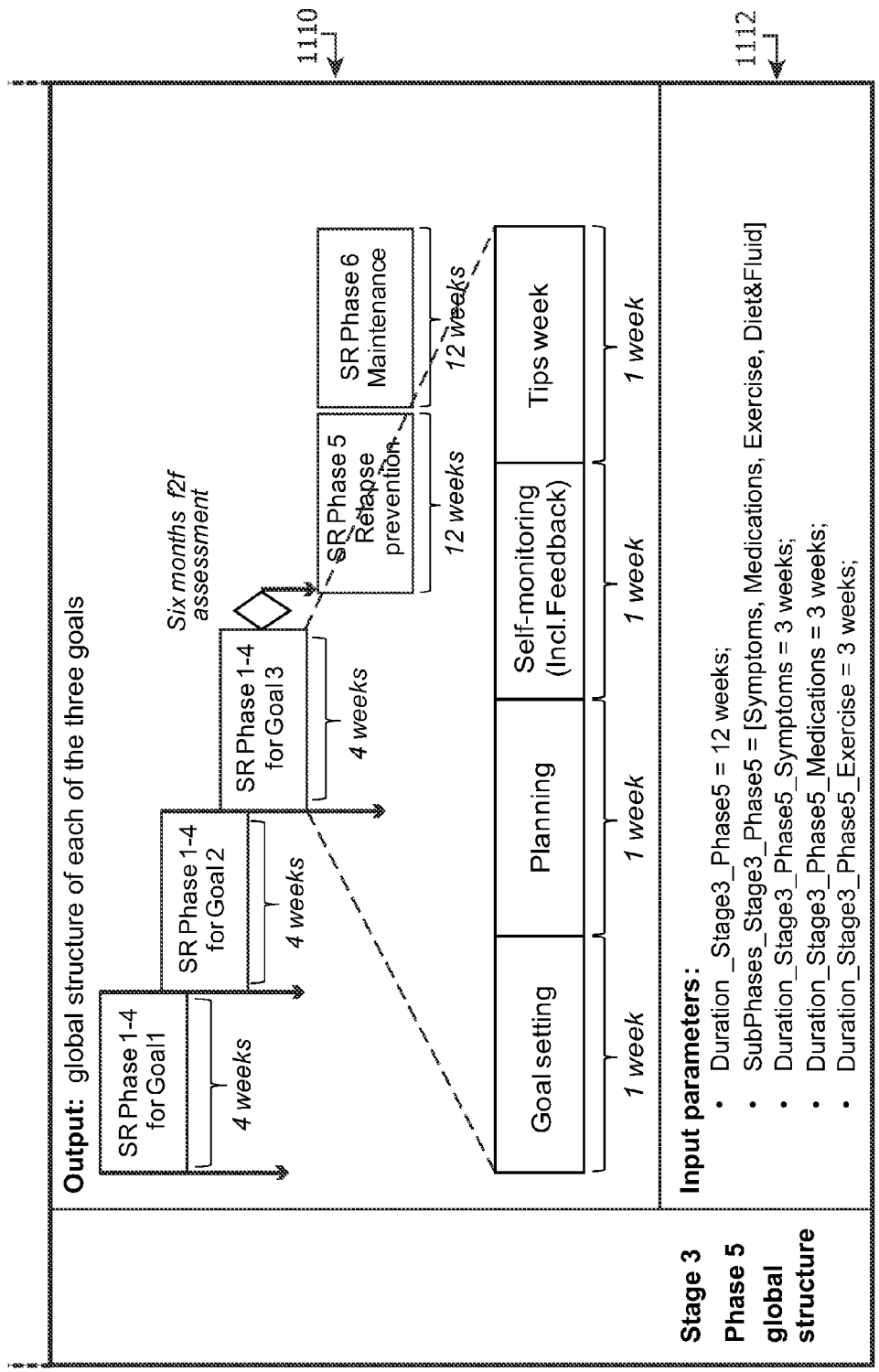
Figures 1, 11C:
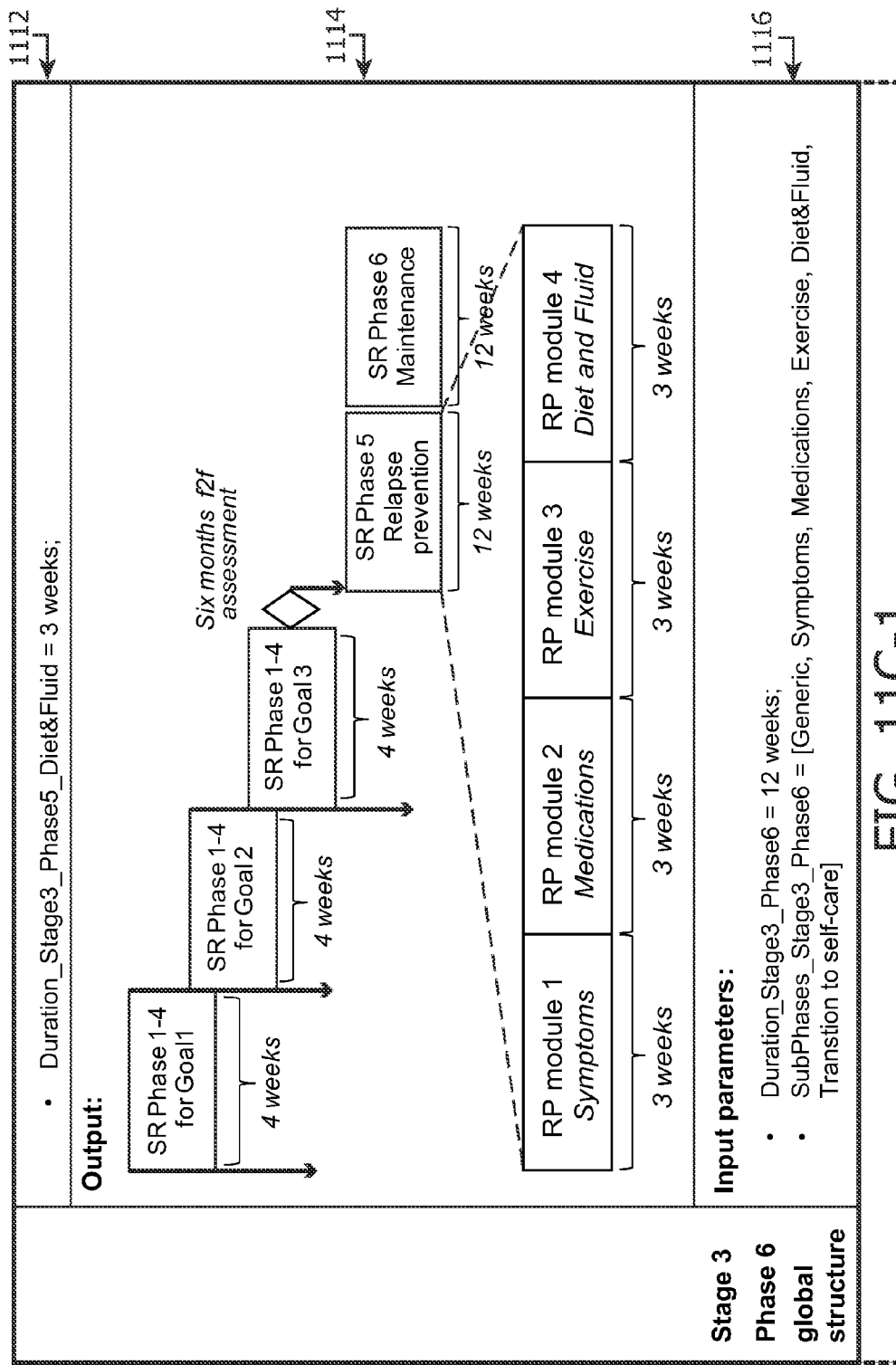
Figures 2, 11C:
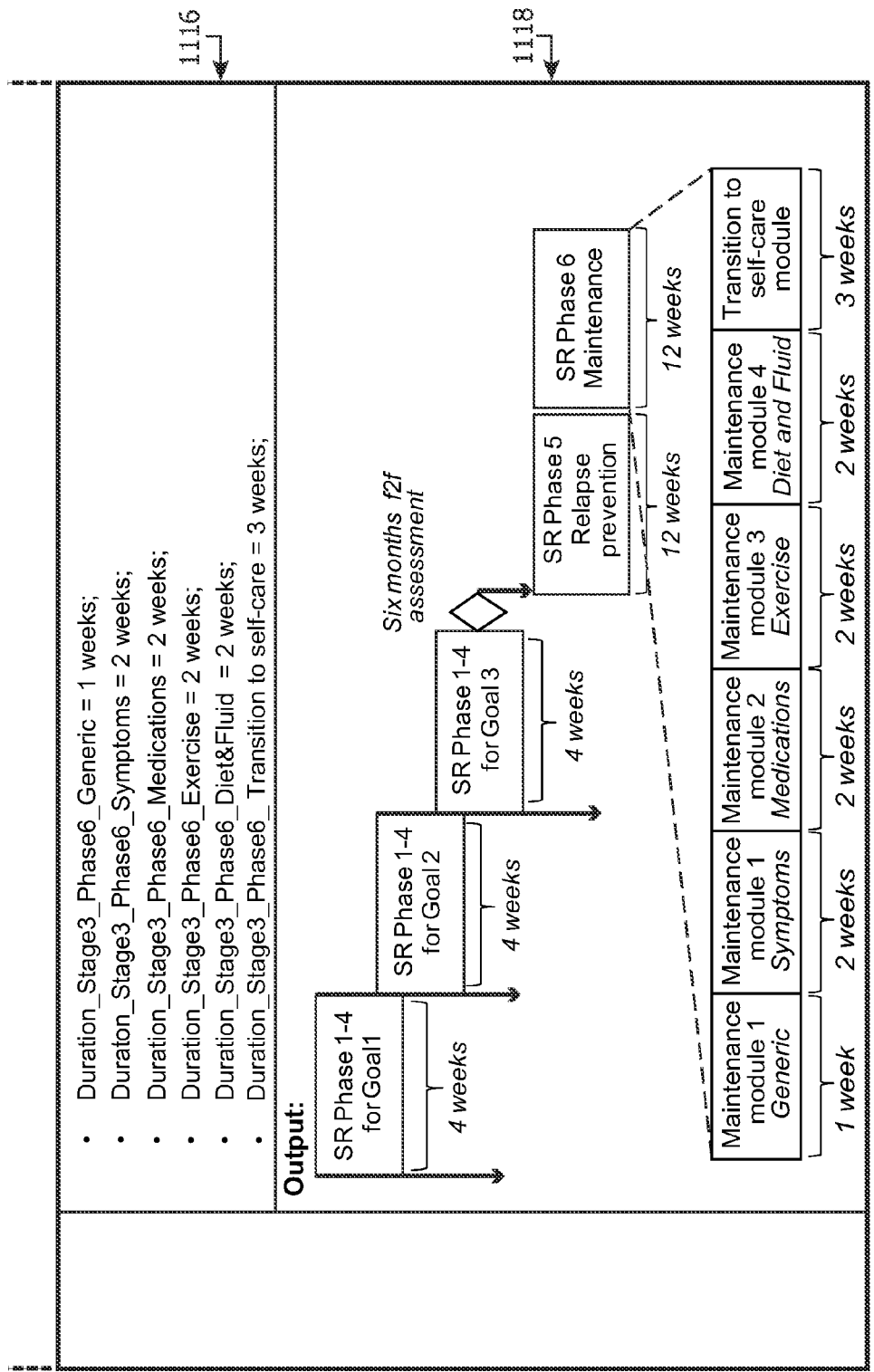
Figure 12B:
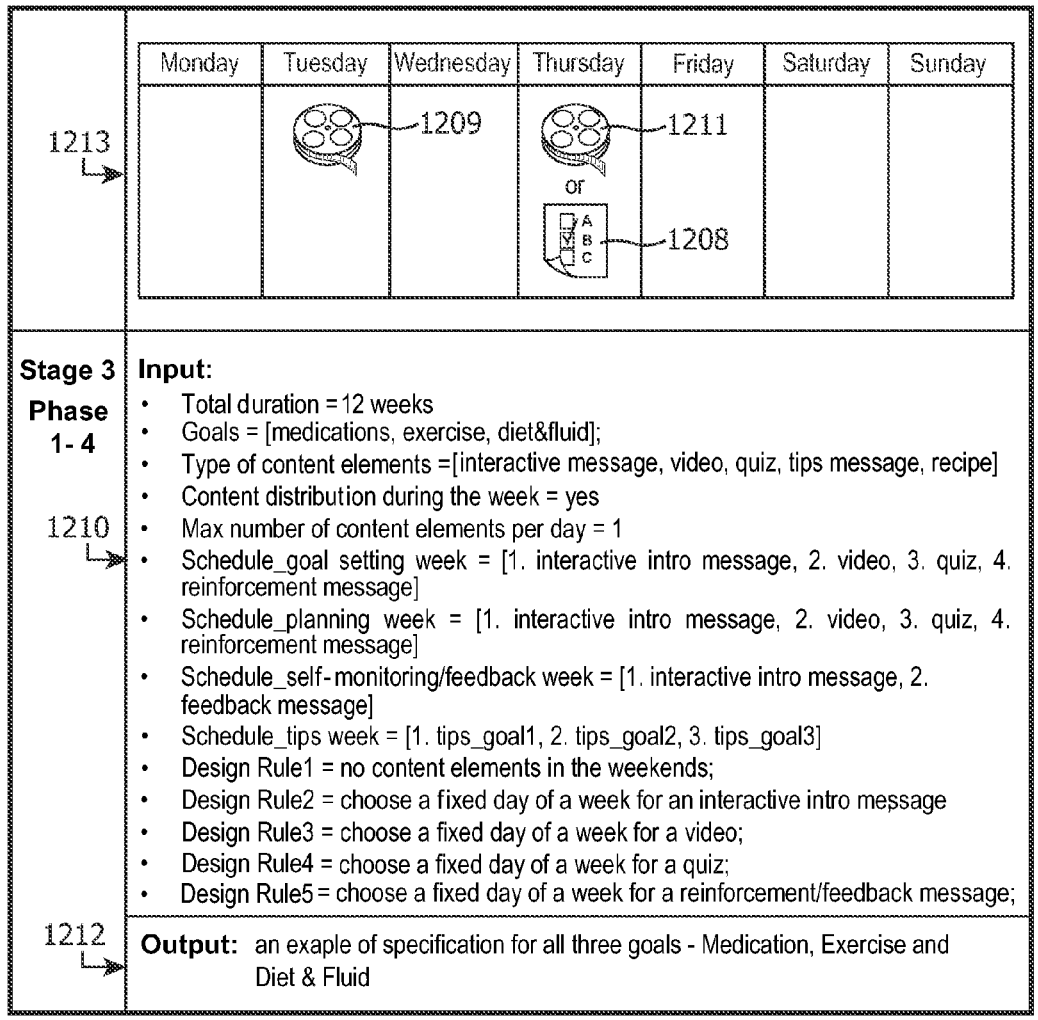
FIG. 12B is a continuation of the table of FIG. 12A.
Figure 12E:
FIG. 12E is a continuation of the table of FIG. 12A, 12B, 12C, and 12D.

FIG. 10 illustrates a library 1000 of multimedia content. FIG. 10 shows the different types of content elements in this library 1000. Within the library 1000 are vital charts 1002, educational videos 1004, messages 1006 and quizzes and/or surveys 1008. Vital charts 1002 are charts which show the value of a vital sign measurement for a period of time. In this FIG. different types of messages 1006 are also shown: tips 1010, interactive messages 1012 and recipes 1014.

FIGS. 11A-1, 11A-2, 11B-1, 11B-2, 11C-1, and 11C-2 are a single table which illustrates step 708 of FIG. 7 in greater detail. This table illustrates how the global structure of the stages and the phases of the stages are designed. In row 1100 the input parameters for the overall design of the coaching plan are designed. In this example the coaching plan lasts for 50 weeks. There are three stages—an introduction, a medical entertainment education stage and a self-regulation stage. The introduction lasts for two weeks. The medical entertainment education stage lasts for 12 weeks and the self-regulation stage lasts for 36 weeks. The self-regulation stage is divided into six phases. The first is a goal setting phase, next is a planning phase, followed by a self-monitoring phase, feedback phase, relapse prevention phase and finally a maintenance phase. Row 1102 shows a graphic which illustrates the overall structure or time line of the coaching plan. Such a display may be presented to a physician to approve or to edit. Row 1104 shows input parameters which are used for the global design of the self-regulation stage. The time used by each of the six phases of the self-regulation stage are detailed. Row 1106 shows a graphic which further details the global structure of the self-regulation stage. Such a graphic may be displayed for a physician or healthcare professional to approve or to modify using the graphical user interface.

Row 1108 shows parameters used to design a global structure of the first four phases of the self-regulation stage. Row 1110 illustrates the structure defined in row 1108 using a graphic. Such a graphic may be used by a physician or a healthcare professional to approve the coaching plan and/or to edit it using the graphical user interface. Rows 1108 and 1110 illustrate the global structure for phases 1-4 of the self-regulation stage. In phases 1-4 goal setting, planning, self-motivation and feedback are addressed. In row 1112 the global structure of phase 5 of the self-regulation stage is described. Phase 5 is relapse prevention. Four sub-phases are defined within phase 5. These sub-phases are modules which are designed to last for three weeks. These cover symptoms, medications, exercise and diet and fluid. Row 1114 shows a graphic which illustrates the design of phase 5 of the self-regulation stage. Such a graphic may be displayed on a graphical user interface for physician approval and/or to receive modifications via a graphical user interface. Row 1116 illustrates the design of phase 6 of the self-regulation stage. During phase 6 generic information, symptoms, medications, exercise, diet and fluid and transition to self care are addressed. The duration of each of these sub-phases is also defined in row 1116. Row 1118 shows a graphical representation of the design of the phase of the self-regulation stage. Such a graphic may be used for physician approval and/or modification using the graphical user interface.

FIGS. 12A, 12B, 12C, 12D, and 12E contain a table which illustrate in detail step 710 of FIG. 7. Row 1200 shows the duration and rules for designing content elements during the first stage of the coaching plan. Row 1202 is shown a calendar for weeks 1 and 2 in the introductory stage. On Monday of the first week, a content element comprising a video clip 1201A and an introductory message 1201B are delivered to the patient. On Tuesday of the first week video 1203 is displayed to the patient. On Thursday of the first week video 1205 is displayed to the patient. During the second week, video 1206 is displayed to the patient on Tuesday and video 1207 is displayed to the patient on Thursday.

Row 1204 shows the design rules for the distribution of content during stage 2 of the coaching plan which is the medical entertainment and education stage. 1213 shows an example of a plan for one week of stage 2. It can be seen that on Tuesday a multimedia content element 1209 is scheduled. On Thursday there is either a video 1211or a quiz 1208 scheduled.

Row 1210 contains rules for the distribution of content and multimedia elements during phases 1-4 of the self-regulation stage. The resulting plan is shown as a calendar in row 1212. This calendar shows four weeks of time. On the first Monday there is an interactive message 1214 which discusses goal setting, choice and introduction. On the first Tuesday, there is a video 1215 scheduled. On the first Thursday there is a goal setting quiz 1216. On the first Friday there is a message 1218 which is an engaging reinforcement message. On the second Monday there is an interactive message which introduces planning 1220. On the second Tuesday, there is a video 1221 scheduled. On the second Thursday there is a planning quiz 1222. On the second Friday there is an engaging reinforcement message 1224. On the third Monday there is an interactive message which is an introduction to self-monitoring 1226. On the third Friday there is an interactive feedback message 1228. On the fourth Monday there is a message 1230 which gives tips on activity. On the fourth Wednesday there is a message 1232 which gives a tip on diet. On the fourth Friday there is a message 1234 which gives a tip on medications.

Row 1236 shows rules for distribution of content during phase 5 which is relapse prevention for the self-regulation stage. In row 1238 a calendar is shown which displays the results of the distribution of content elements using the rules of row 1236. The calendar shows three weeks of content elements. On the first Monday there is an interactive message 1240 to identify barriers. On the first Tuesday there is a multimedia element such as video 1241. On the first Thursday there is a quiz 1243. On the first Friday there is a reinforcement message 1242. On the Monday of the second week there is a tip 1244 on an identified barrier or barriers. On Thursday of the second week there is an additional tip 1245 on an identified barrier or barriers. On Monday of the third week there is an additional tip 1247 on an identified barrier or barriers. On Thursday of the third week there is an additional tip 1251 on an identified barrier or barriers.

Row 1246 shows rules for the distribution of content elements during phase 6 which is maintenance for the self-regulation stage. In row 1248 three different calendars are shown. The first calendar 1250 shows an example of a specification for a generic module or sub-phase. This is for a single week. During Tuesday a multimedia clips such as a film 1253 is displayed to the patient. During Thursday an additional multimedia clips such as a film 1255 is displayed to the patient. On Monday an interactive quiz 1252 which introduces maintenance is delivered to the patient. On Friday a reinforcement message 1254 is delivered to the patient.

The second calendar 1256 shows an example of a specification for modules or sub-phases of the self-regulation stage. Calendar 1256 shows two weeks. On Monday of the first week a message 1257 with a tip on a benefit is delivered to the patient. On Thursday of the first week a message 1258 with an additional tip on a benefit is delivered to the patient. Similarly, On Monday of the second week a message 1259 with an additional tip on a benefit is delivered to the patient. On Thursday of the second week a message 1261 with an additional tip on a benefit is delivered to the patient.

The third calendar 1260 illustrates an example of a specification for the transition to self-care. This calendar 1260 shows three weeks. During the first Monday an interactive message 1262 which introduces aftercare is delivered to the patient. On the first Wednesday a quiz 1264 on self-monitoring and vital signs is sent to the patient. On the first Friday a message 1266 which contains a tip on the benefit of self-monitoring is delivered to the patient. On the second Tuesday a quiz 1268 on social support is delivered to the patient. On the second Thursday a message 1270 which contains a tip on the benefit of social support is delivered to the patient. On the third Friday a quiz 1272 which is a closing quiz is delivered to the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

LIST OF REFERENCE NUMERALS

200 computing device
202 application hosting device
204 health professional interface
206 user interface and/or feedback device
208 patient
210 blood pressure measurement device
212 scale
214 urine test strip reader
216 urine sample
218 display
220 processor
222 storage
224 memory
226 instructions for performing method
228 care plan
230 instruction for performing method
232 care plan
234 multi-media library
236 server
238 storage
240 multi-media library
242 computer memory
246 care plan
248 multi-medial library 250 library of care plan executables
252 regulatory guidelines database
254 behavioral models database
256 determinants of compliance database
258 care plan
260 display
262 graphical user interface of wizard
264 check boxes
266 continue button
268 list of psychological determinants
600 physical components of remote patient management system
602 functional organization of software components
604 diagnostic medical device or devices
606 feed back device
608 computer implementable instructions
610 coaching plan authoring tool
612 coaching plan compiler
614 coaching plan linker
616 determinants of compliance data base
618 behavioral models data base
620 guidelines data base
622 coaching plan data base
624 multi-media library
626 care plan executables data base
1000 multi-media library
1002 vitals charts
1004 educational videos
1006 messages
1008 quizzes and surveys
1010 tips
1012 interactive messages
1014 recipes
1201A multimedia content element
1201B message
1203 multimedia content element
1205 multimedia content element
1206 multimedia content element
1207 multimedia content element
1208 quiz
1209 multimedia content element
1211 multimedia content element
1214 interactive message
1215 multimedia content element
1216 quiz
1218 interactive message
1220 interactive message
1221 multimedia content element
1222 quiz
1224 interactive message
1226 interactive message
1228 interactive message
1230 message
1232 message
1234 message
1240 interactive message
1241 multimedia content element
1242 message
1243 quiz
1244 message
1245 message
1247 multimedia content element
1251 multimedia content element
1252 interactive message
1253 multimedia content element
1254 message
1255 multimedia content element
1257 message
1258 message
1259 message
1261 message
1262 interactive message
1264 quiz
1266 message
1268 quiz
1270 message
1272 quiz

The invention claimed is:

1. A computer-implemented method for creating a care plan, the method comprising:
displaying, by a display device, a list of psychological determinants;
receiving, by a processor, a selection of a group of psychological determinants chosen from the list of psychological determinants;
generating, by the processor, a list of behavioral models using the group of psychological determinants;
receiving, by the processor, a selection of at least one selected behavioral model from the list of behavioral models;
determining, by the processor, a time line for a global structure of a coaching plan using the at least one selected behavioral model, wherein the time line defines a stage of the coaching plan for each of the at least one selected behavioral model, wherein each stage specifies unresolved symbolic links representing multi-media content;
compiling, by the processor, a coaching object file using the time line, wherein the coaching object file comprises the unresolved symbolic links;
linking, by the processor, the coaching object file to a library of multi-media content to resolve the unresolved symbolic links; wherein linking the coaching object file creates the coaching plan;
integrating, by the processor, the coaching plan into the care plan; and
writing, by the processor, the care plan to a computer-readable storage medium.

2. The computer-implemented method of claim 1, wherein the method further comprises the step of receiving physician approval before compiling the coaching plan, whereby the coaching object file becomes a physician approved coaching object file; wherein the method further comprises the step of receiving physician approval of the multi-media content; and wherein the coaching plan is physician approved by virtue of the physician approved coaching object file and the multi-media content.

3. The computer-implemented method of claim 1, wherein a behavioral model comprises a set of psychological determinants, wherein a behavioral model is selected for the list of behavioral models if the selection of psychological determinants contains more than a predetermined number of psychological determinants belonging to the group of psychological determinants.

4. The computer-implemented method of claim 1, wherein the determination of the time line comprises using defined rules.

5. The computer-implemented method of claim 4, wherein the method further comprises receiving a modification to the defined rules.

6. The computer-implemented method of claim 4, wherein the defined rules comprise any one of the following: regional regulatory rules, national regulatory rules, and local practice guidelines.

7. The computer-implemented method of claim 1, wherein the instructions comprise rules for displaying multimedia content using measurements by the remote patient management system as a trigger.

8. The computer-implemented method of claim 1, wherein the instructions comprise commands for displaying the contents of each stage.

9. The computer-implemented method of claim 8, wherein the instruction comprise commands for receiving a modification to the contents of each stage.

10. The computer-implemented method of claim 1, wherein the multimedia library comprises any one of the following: charts showing vital sign trends, educational videos, quizzes, surveys, messages, tips, interactive messages, checklists, medication checklists, symptoms checklists, games, games-for-health, and recipes.

11. The computer-implemented method of claim 1, wherein the time line further specifies an introductory stage; wherein the introductory stage is a stage that occurs before all other stages on the timeline; wherein the introductory stage is not specified by one of the at least one selected behavioral model.

12. The computer-implemented method of claim 1, wherein the step of compiling the coaching object file comprises using a set of constraints which limit the duration of the coaching plan.

13. The computer-implemented method of claim 1, wherein the method further comprises the step of receiving a list of psychological determinants; wherein the method further comprises receiving a group of behavioral models; wherein the list of behavioral models is chosen from the group of behavioral models; wherein each of the group of behavioral models comprises a definition of which psychological determinants it addresses; wherein the method further comprises the step of receiving a library of multi-media content; wherein the library of multimedia content comprises multimedia elements; wherein each multimedia element comprises a reference to which of the group of behavioral models it addresses; wherein each multimedia element comprises a reference to which of the list of psychological determinants it addresses; and wherein the behavioral models define events in a stage of the coaching plan which are chosen using a behavioral modification model.

14. The computer-implemented method of claim 1, wherein the remote patient management system comprises an application hosting device; and wherein the hosting device comprises at least one diagnostic medical device.

15. The computer-implemented method of claim 14, wherein the instructions comprise rules that trigger an element of the library of multi-media content when a scheduled measurement of a vital sign by the at least one diagnostic medical device is not received.

16. The computer-implemented method of claim 1, wherein the instructions comprise rules that trigger an element of the library of multi-media when a measurement of a vital sign by the at least one diagnostic medical device is outside of a predetermined range.

17. A non-transitory computer-readable storage medium containing instructions that when executed by a processor perform a method for creating a care plan the method comprising:
displaying a list of psychological determinants;
receiving a selection of a group of psychological determinants chosen from the list of psychological determinants;
generating a list of behavioral models using the group of psychological determinants;
receiving a selection of at least one selected behavioral model from the list of behavioral models;
determining a time line for a global structure of a coaching plan using the at least one selected behavioral model, wherein the time line defines a stage of the coaching plan for each of the at least one selected behavioral model, wherein each stage specifies unresolved symbolic links representing multi-media content;
compiling a coaching object file using the time line, wherein the coaching object file comprises the unresolved symbolic links;
linking the coaching object file to a library of multi-media content to resolve the unresolved symbolic links; wherein linking the coaching object file creates the coaching plan;
integrating the coaching plan into the care plan; and
writing the care plan to a second computer-readable storage medium.

18. The non-transitory computer-readable storage medium of claim 17, wherein the instructions on the non-transitory computer-readable-storage medium contain instruction for implementing the method using a wizard displayed on a graphical user interface.

19. A remote patient management system comprising:
an application hosting device, wherein the application hosting device comprises a feedback device, wherein the application hosting device further comprises at least one diagnostic medical device;
a health care provider interface;
a computing device comprising at least one processor;
a first computer-readable storage medium containing instruction that when executed by the at least one processor cause the computing device to perform a method of manufacturing a second computer-readable storage medium containing instructions for execution by a remote patient management system, wherein the remote patient management system comprises at least one processor for executing the instructions, wherein execution of the instructions causes the remote patient management system to execute a coaching plan, the method comprising:
displaying a list of psychological determinants;
receiving a selection of a group of psychological deteiininants chosen from the list of psychological determinants;
generating a list of behavioral models using the group of psychological determinants;
receiving a selection of at least one selected behavioral model from the list of behavioral models;
determining a time line for a global structure of the coaching plan using the at least one selected behavioral model, wherein the time line defines a stage of the coaching plan for each of the at least one selected behavioral model, wherein each stage specifies unresolved symbolic links representing multi-media content;
compiling a coaching object file using the time line, wherein the coaching object file comprises the unresolved symbolic links;
linking the coaching object file to a library of multi-media content to resolve the unresolved symbolic links; wherein linking the coaching object file creates the coaching plan;
integrating the coaching plan into the care plan; and writing the care plan to the second computer-readable storage medium.

20. The remote patient management system of claim 19, wherein the application hosting device comprises at least one processor; and wherein instructions of the second computer-readable storage medium is executed by the application hosting device.

\* \* \* \* \*